United States Patent
Mulshine et al.

(10) Patent No.: US 6,500,625 B1
(45) Date of Patent: Dec. 31, 2002

(54) METHODS FOR DIAGNOSING CANCER OR PRECANCER BASED UPON HNRNP PROTEIN EXPRESSION

(75) Inventors: James L. Mulshine, Bethesda, MD (US); Melvyn S. Tockman, Tampa, FL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/542,552

(22) Filed: Apr. 3, 2000

Related U.S. Application Data

(60) Continuation of application No. 09/255,609, filed on Feb. 19, 1999, which is a division of application No. 08/538,711, filed on Oct. 2, 1995, now Pat. No. 5,994,062.

(51) Int. Cl.$^7$ .................. G01N 33/574; G01N 33/567; G01N 33/53; G01N 33/537; C12Q 1/00
(52) U.S. Cl. .................. 435/7.23; 435/4; 435/7.21; 435/7.92; 435/7.93; 436/63; 436/64; 436/86; 436/174; 436/501; 530/300; 530/327; 530/328
(58) Field of Search .................. 435/4, 7.21, 7.23, 435/7.92, 7.93; 436/501, 63, 64, 174, 86; 530/300, 327, 328

(56) References Cited

U.S. PATENT DOCUMENTS

| | | | |
|---|---|---|---|
| 4,569,788 A | 2/1986 | Mulshine et al. | 260/112 R |
| 4,683,195 A | 7/1987 | Mullis et al. | 435/6 |
| 5,683,202 A | 7/1987 | Mullis | 435/91 |
| 5,194,599 A | 3/1993 | Froehler | 535/26.72 |
| 5,256,775 A | 10/1993 | Froehler | 536/25.6 |
| 5,264,562 A | 11/1993 | Matteucci | 536/23.1 |
| 5,455,159 A | 10/1995 | Mulshine et al. | 435/7.23 |
| 6,025,540 A * | 2/2000 | Hansson | |

OTHER PUBLICATIONS

Amino acid database sheet, Sequence 2 of U.S. Patent 6,025,540. (2000).*

Ishikawa et al., "Nuclear Proteins that Bind the Pre–mRNA 3' Splice Site Sequence r(UUAG/G) and the Human Telemeric DNA Sequence d(TTAGGG)n," *Mol. Cell. Biol.* 13(7):4301–4310 (Jul., 1993).

Martinez, et al., "Expression of Peptidyl–Glycin α–Amidating Mono–Oxygenase (PAM) Enzymes in Morphological Abnormalities Adjacent to Pulmonary Tumors," *American Journal of Pathology*, 149(2):707–716 (Aug., 1996).

Mayeda et al., "Function of conserved domains of hnRNP A1 and other hnRNP A/B proteins," *The EMBO Journal*, 13(22):5483–5495 (1994).

Scott et al., "Prospective Trial Evaluating Immunocytochemical–based Sputum Techniques for Early Lung Cancer Detection: Assays for Promotion Factors in the Bronchila Lavage," *Journal of Cellular Biochemistry*, Supplement 17F:175–183 (1993).

Tang et al., Self–stabilized antisense oligodeoxynucleotide phosphorothioates: properties and anti–HIV activity, *Nucleic Acids Res.*, 21(11):2729–2735 (1993).

Zhou, et al., "Purification and Characterization of a Protein that Permits Early Detection of Lung Cancer," *The Journal of Biological Chemistry*, 271(18):10760–10766 (May, 1996).

Anderson et al., "A two–dimensional gel database of rat liver proteins useful in gene regulation and drug effects studies," *Electrophoresis*, 12:907–930 (1991).

Biamonti, "Human hnRNP Protein A1 Gene Expression," *J. Mol. Biol.*, 230:77–89 (1993).

Biamonti, et al., "Two homologous genes, originated by duplication encode the human hnRNP proteins A2 and A1," *Nucleic Acid Res.*, 22(11):1996–2002 (Jun., 1994).

(List continued on next page.)

Primary Examiner—Anthony C. Caputa
Assistant Examiner—Alana M. Harris
(74) Attorney, Agent, or Firm—Leydig, Voit & Mayer, Ltd.

(57) ABSTRACT

The present invention is a purified and isolated epithelial protein, peptide and variants thereof whose increased presence in an epithelial cell is indicative of precancer. One epithelial protein which is an early detection marker for lung cancer was purified from two human lung cancer cell lines, NCI-H720 and NCI-H157. Using a six-step procedure, the epithelial protein was purified using a Western blot detection system under both non-reducing and reducing conditions. Purification steps included anion exchange chromatography, preparative isoelectric focusing, polymer-based $C_{18}$ HPLC and analytic $C_4$ HPLC. After an approximately 25,000 fold purification the immunostaining protein was >90% pure as judged by Coomassie blue staining after reducing SDS-PAGE. The primary epithelial protein shares some sequence homology with the heterogeneous nuclear ribonucleoprotein (hnRNP) A2. A minor co-purifying epithelial protein shares some sequence homology with the splice variant hnRNP-B1. Molecular analysis of primary normal bronchial epithelial cell cultures demonstrated low levels of epithelial protein expression, consistent with immunohistochemical staining of clinical samples, and an increased level of expression in most lung cancer cells. The epithelial protein is a marker of epithelial transformation in lung, breast, bone, ovary, prostate, kidney, melanoma and myeloma and may be casual in the process of carcinogenesis. Methods are provided for monitoring the expression of the epithelial protein, peptides and variants using molecular and immunological techniques as a screen for precancer and cancer in mammals.

11 Claims, 17 Drawing Sheets

OTHER PUBLICATIONS

Boffe et al., "Distribution of $N^G$, $N^G$–Dimethylarginine in Nuclear Protein Fractions," *Biochemical and Biophysical Research Communications*, 74(3):969–976 (1977).

Burd, et al., "Conserved Structures and Diversity of Functions of RNA–Binding Proteins," *Science* 265:615–621 (Jul. 29, 1994).

Burd, et al., "Primary structures of the heterogeneous nuclear ribonucleoprotein A2, B1 and C2 proteins: A diversity of RNA binding proteins is generated by small peptide inserts," *Proc. Nat'l Sci. USA* 86:9788–9792 (1989).

Carter et al., "Relationship of morphology of clinical presentation in ten cases of early squamous carcinoma of the lung," *Cancer*, 37:1389–1396 (1976).

Dreyfuss, et al., "hnRNP Proteins and the Biogenesis of mRNA," *Ann. Res. Biochem*, 62:289–321 (1993).

Ganju, "CD 10/NEP in Non–small Cell Lung Carcinomas," *J. Clin. Invest.* 94:1784–1791 (1994).

Ishikawa, et al., "Nuclear Proteins that Bind the Pre–mRNA 3' Splice Site Sequence r(UUAG/G) and the Human Telemeric DNA Sequence d(TTAGGG)n," *Mol. Cell. Biol.* 13:4301–4310 (1993).

Jensen et al., "Clara cell 10KD protein mRNA in normal and atypical regions of human respiratory epithelium," *Int. J. Cancer*, 58:629–637 (1994).

Karn et al., Characterization of the Non–histone Nuclear Proteins Associated with Rapidly Labeled Heterogeneous Nuclear RNA, *The Journal of Biological Chemistry*, 252(20):7307–7322 (Oct., 1977).

Katz, et al., "AU–A, an RNA–binding activity distinct from hnRNP A1, is selective for AUUUA repeats and shuttles between the nucleus and the cytoplasm," *Nucleic Acid Res.*, 22(2):238–246 (1994).

Krajewski, "Investigation of the subcellular distribution of the bcl–2 oncoprotein: Residence in the Nuclear Envelope, Endoplasmic Reticulum and Outer Mitrochondrial Membranes," *Cancer Res.*, 53:4701–4714 (1993).

Kumar et al., "Purification and domain Structure of Core hnRNP Proteins A1 and A2 and Their Relationship to Single–Stranded DNA–binding Proteins," *The Journal of Biological Chemistry*, 261(24):11266–11273 (Aug. 25, 1986).

Martinez, et al., "Expression of Peptidyl–Glycine ∀–Amidating Mono–Oxygenase (PAM) Enzymes in Morphological Abnormalities Adjacent to Pulmonary Tumors," *American Journal of Pathology*, 149 (2): 707–716 (Aug., 1996).

Martinez, et al., "Non–radioactive Localization of Nucleic Acids by Direct in Situ PCR and In Situ RT–PCR in Paraffin–Embedded Sections", *The Journal of Histochemistry and Cytochemistry*, 43(8):739–747 (1995).

McKay, et al., "hnRNP A2/B1 binds specifically to single stranded vertebrate telemeric repeat TTAGGGn," *Nucleic Acids Res.*, 20:6461–60 (1992).

Medzihradszky et al., "Characterization of Protein N–Glycosylation by Reversed–Phase Microbore Liquid Chromatography/Electrospray Mass Spectrometry, Complementary Mobile Phases, and Sequential Exoglycosidase Digestion," *J Am Soc. Mass Spectrom*, 5:350–358 (1994).

Merrill et al. "High Pressure Liquid Chromatography Purification of UP1 and UP2, Two Related Single stranded Nucleic Acid–binding Proteins from Calf Thymus," *The Journal of Biological Chemistry* 261(2):878–883 (Jan. 15, 1986).

Mulshine et al., "Molecular Markers in Early Cancer Detection," *Chest Supplement*, 107(6):280S–286S (Jun., 1995).

Mulshine et al., "Monoclonal Antibodies that distinguish Non–Small Cell from Small–Cell Lung Cancer," *The Journal of Immunology*, 131(1):497–502 (Jul., 1983).

Naisell et al., "Cytological studies in man and animals on development of bronchogenic carcinoma. In: Lung Carcinomas," E. McDowell (eds)., pp. 207–242, New York: Churchill Livingstone (1987).

Padmapriya et al., "Synthesis of Oligodeoxynucleoside Methylphosphonothioates," *Bio Org. & Med. Chem. Lett.*, 3:761–764 (1993).

Pinol–Roma et al., "Shuttling of pre–mRNA binding proteins between nucleous and cytoplasm," *Nature* 355:730–732 (1992).

Risio, "Cell Proliferation in Colorectal Tumor Progression: An Immunohistochemical Approach to Intermediate Biomarkers," *J. Cell. Biochem., Suppl. 16G*:79–87 (1992).

Saccomanno et al., "Cytology of the lung in reference to irritant, individual sensitivity and healing," *Acta Cytol*, 14:377–380 (1970).

Saccomanno et al., "Development of carcinoma of the lung as reflected in exfoliated cells," *Cancer* 33:256–270 (1974).

Saccone, et al., "Assignment of the Human Heterogeneous Nuclear Ribonucleoprotein A1 Gene (HNRPA1) to Chromosome 12q13.1 by cDNA Competitive in Situ Hybridization," *Genomics Jan*:12(1):171–174 (1992).

Shaw, et al., "Individualized chemotherapy for patients with non–small cell lung cancer determined by prospective identification of neuroendocrine markers and in vitro drug sensitivity testing," *Cancer Research* 53:5180–5187 (1993).

Sozzi et al., "Cytogenetic abnormalities and overexpression of receptors for growth factor in normal bronchial epithelium and tumor samples of lung cancer patients," *Cancer Res.*, 51:400–404 (1991).

Spector, "Nuclear organization of pre–mRNA processing," *Curr. Opin. Cell. Biol.* 5:442–447 (1993).

Tang et al., "Self–stabilized antisense oligodeoxynucleotide phosphorothioates: properties and anti–HIV activity," *Nucleic Acids Res.*, 21(11):2729–2735 (1993).

Temsamani et al., "Capped Oligodeoxynucleotide Phosphorothioates," *Ann. N.Y. Acad. Sci.*, 660:318–320 (1992).

Tockman et al., "Consideration in Bringing a Cancer Biomarker to Clinical Application," *Cancer Research (Suppl.)*, 52:2711s–2718s (May, 1992).

Tockman et al., "Cytometric Validation of Immunocytochemical Observations in Developing Lung Cancer," *Diagnostic Cytopathology*, 9(6):615–622 (1993).

Tockman et al., "Sensitive and Specific Monoclonal Antibody Recognition of Human Lung Cancer Antigen on Preserved Sputum Cells: A New Approach to Early Lung Cancer Detection," *Journal of Clinical Oncology*, 6(11):1685–1693 (Nov., 1988).

Tockman et al., "The Early Detection of Second Primary Lung Cancers by Sputum Immunostaining," *Chest* 106(6):385S–390S (Dec., 1994).

Williams et al., "Amino acid sequence of the UP1 calf thymus helix–destabilizing protein and its homology to an analogous protein from mouse myeloma," *Proc. Natl. Acad. Sci. USA*, 82:5666–5670 (1985).

Wulf et al., "Improvement of Fluorescence In Situ Hybridization (RNA–FISH) on Human Paraffin Sections by Propidium Iodid Counterstaining," *BioTechniques*, 19(3) (Sep., 1995).

Zhou, et al., "Purification and Characterization of a Protein that Permits Early Detection of Lung Cancer," *The Journal of Biological Chemistry*, 271(18):10760–10766, (1996).

* cited by examiner

FIG. 1

| | | |
|---|---|---|
| 1 | ATGTCTAAGTCAGAGTCTCCTAAAGAGCCCGAACAGCTGA | A1-cds (SEQ. ID. NO. 9) |
| 1 | ATG---------GAG------AGAGAAAAGGAACAGTTCC | A2 cds (SEQ. ID. NO. 10) |
| 41 | GGAAGCTCTTCATTGGAGGGTTGAGCTTTGAAACAACTGA | A1-cds |
| 26 | GTAAGCTCTTTATTGGTGGCTTAAGCTTTGAAACCACAGA | A2 cds |
| 81 | TGAGAGCCTGAGGAGCCATTTTGAGCAATGGGGAACGCTC | A1-cds |
| 66 | AGAAAGTTTGAGGAACTACTACGAACAATGGGGAAAGCTT | A2 cds |
| 121 | ACGGACTGTGTGGTAATGAGAGATCCAAACACCAAGCGCT | A1-cds |
| 106 | ACAGACTGTGTGGTAATGAGGGATCCTGCAAGCAAAAGAT | A2 cds |
| 161 | CTAGGGGCTTTGGGTTTGTCACATATGCCACTGTGGAGGA | A1-cds |
| 146 | CAAGAGGATTTGGTTTTGTAACTTTTTCATCCATGGCTGA | A2 cds |
| 201 | GGTGGATGCAGCTATGAATGCAAGGCCACACAAGGTGGAT | A1-cds |
| 186 | GGTTGATGCTGCCATGGCTGCAAGACCTCATTCAATTGAT | A2 cds |
| 241 | GGAAGAGTTGTGGAACCAAAGAGAGCTGTCTCCAGAGAAG | A1-cds |
| 226 | GGGAGAGTAGTTGAGCCAAAACGTGCTGTAGCAAGAGAGG | A2 cds |
| 281 | ATTCTCAAAGACCAGGTGCCCACTTAACTGTGAAAAAGAT | A1-cds |
| 266 | AATCTGGAAAACCAGGGGCTCATGTAACTGTGAAGAAGCT | A2 cds |
| 321 | ATTTGTTGGTGGCATTAAAGAAGACACTGAAGAACATCAC | A1-cds |
| 306 | GTTTGTTGGCGGAATTAAAGAAGATACTGAGGAACATCAC | A2 cds |
| 361 | CTAAGAGATTATTTTGAACAGTTTGGAAAAATTGAAGTGA | A1-cds |
| 346 | CTTAGAGATTACTTTGAGGAATATGGAAAAATTGATACCA | A2 cds |
| 401 | TTGAAATCATGACTGACCGAGGCAGTGGCAAGAAAAAGGG | A1-cds |
| 386 | TTGAGATAATTACTGATAGGCAGTCTGGAAAGAAAAGAGG | A2 cds |
| 441 | CTTTGCCTTTGTAACCTTTGACGACCATGACTCCGTGGAT | A1-cds |
| 426 | CTTTGGCTTTGTTACTTTTGATGACCATGATCCTGTGGAT | A2-cds |
| 481 | AAGATTGTCATTCAGAAATACCATACTGTGAATGGCCACA | A1-cds |
| 466 | AAAATCGTATTGCAGAAATACCATACCATCAATGGTCATA | A2 cds |
| 521 | ACTGTGAAGTTAGAAAAGCCCTGTCAAAGCAAGAGATGGC | A1-cds |
| 506 | ATGCAGAAGTAAGAAAGGCTTTGTCTAGACAAGAAATGCA | A2 cds |
| 561 | TAGTGCTTCATCCAGCCAAAGAGGTCGAAGTGGTTCTGGA | A1-cds |
| 546 | GGAAGTTCAG---AGTTCTAGGAGTGGAAGAGGA----GGC | A2 cds |
| 601 | AACTTTGGTGGTGGTCGTGGAGGTGGTTTCGGTGGGAATG | A1-cds |
| 580 | AACTTTGGCTTTGGGGATTCACGTGGTGGCGGTGGAAATT | A2 cds |
| 641 | ACAACTTCGGTCGTGGAGGAAACTTCAGTGGTCGTGGTGG | A1-cds |
| 620 | TCGGACCAGGACCAGGAAGTAACTTTAGAGGA------GG | A2 cds |
| 681 | CTTTGGTGGCAGCCGTGGTGGTGGTGGATATGGTGGCAGT | A1-cds |
| 654 | ATCTGATGGATATGGCAGTGGACGTGGAT---------TT | A2 cds |
| 721 | GGGGATGGCTATAATGGATTTGGCAA------TGATGGAA | A1-cds |
| 685 | GGGGATGGCTATAATGGGTATGGAGGAGGACCTGGAGGTG | A2 cds |
| 755 | GCAATTTTGGAGGTG------------------------- | A1-cds |
| 725 | GCAATTTTGGAGGTAGCCCCGGTTATGGAGGAGGAAGAGG | A2 cds |

FIG. 2
Human hnRNP A2

```
cgg gtc ccg tgc gga ggt gct cct cgc aga gtt gtt        36
tct cga gca gcg gca gtt ctc act aca gcg cca gga        72
cga gtc cgg ttc gtg ttc gtc cgc gga gat ctc tct       108
cat ctc gct cgg ctg cgg gaa atc ggg ctg aag cga       144
ctg agt ccg cga tgg aga gag aaa agg aac agt tcc       180
gta acg tct tta ttg gtg gct taa gct ttg aaa cca       216
cag aag aaa gtt tga gga act act acg aac aat ggg       252
gaa agc tta cag act gtg tgg taa tga ggg atc ctg       288
caa gca aaa gat caa gag gat ttg gtt ttg taa ctt       324
ttt cat cca tgg ctg agg ttg atg ctg cca tgg ctg       360
caa gac ctc att caa ttg atg gga gag tag ttg agc       396
caa aac gtg ctg tag caa gag agg aat ctg gaa aac       432
cag ggg ctc atg taa ctg tga aga agc tgt ttg ttg       468
gcg gaa tta aag aag ata ctg agg aac atc acc tta       504
gag att act ttg agg aat atg gaa aaa ttg ata cca       540
ttg aga taa tta ctg ata ggc agt ctg gaa aga aaa       576
gag gct ttg gct ttg tta ctt ttg atg acc atg atc       612
ctg tgg ata aaa tcg tat tgc aga aat acc ata cca       648
tca atg gtc ata atg cag aag taa gaa agg ctt tgt       684
cta gac aag aaa tgc agg aag ttc aga gtt cta gga       720
gtg gaa gag gag gca act ttg gct ttg ggg att cac       756
gtg gtg gcg gtg gaa att tcg gac cag gac cag gaa       792
gta act tta gag gag gat ctg atg gat atg gca gtg       828
gac gtg gat ttg ggg atg gct ata atg ggt atg gag       864
gag gac ctg gag gtg gca att ttg gag gta gcc ccg       900
gtt atg gag gag gaa gag gag gat atg gtg gtg gag       936
gac ctg gat atg gca acc agg gtg ggg gct acg gag       972
gtg gtt atg aca act atg gag gag gaa att atg gaa      1008
gtg gaa att aca atg att ttg gaa att ata acc agc      1044
aac ctt cta act acg gtc aat gaa gag gtg gaa act      1080
ttg gtg gta gca gga aca tgg ggg gac cat atg gtg      1116
gag gaa act atg gtc agg agg cag tgg aga agt gtg      1152
ggg gtt atg gtg gga gga gcc gat act gag ctt ctt      1188
cct att tgc cat ggg ctt cac tgt ata aat agg aga      1224
gga tga gag ccc aga ggt aac aga aca gct tca ggt      1260
```

FIG. 2 Continued

```
tat cga aat aca aat gtg aag gaa act ctt atc tca      1296
gtc atg cat aaa tat gca gtg ata tgg cag aag aca      1332
cca gag cag atg cag aga gcc att ttg tga atg gat      1368
tgg att att taa taa cat tac ctt act gtg gag gaa      1404
gga ttg taa aaa aaa atc cct ttg aga cag ttt ctt      1440
agc ttt tta att gtt gtt tct ttc tag tgg tct ttg      1476
taa gag tgt aga agc att cct tct ttg ata atg tta      1512
aat ttg taa gtt tca ggt gac atg tga aac ctt ttt      1548
taa gat ttt tct caa agt ttt gaa aag cta tta gcc      1584
agg atc atg gtg taa taa gac ata acg ttt ttc ctt      1620
taa aaa aat tta agt gcg tgt gta gag tta aga agc      1656
tgt tgt aca ttt atg att taa taa aat aat tct aaa      1692
gga aaa aa                                            1700
```

FIG. 3
Human hnRNP-B1

```
ccg tgc gga ggt gct cct cgc aga gtt gtt tct cga        36
gca gcg gca gtt ctc act aca gcg cca gga cga gtc        72
cgg ttc gtg ttc gtc cgc gga gat ctc tcc cat ctc       108
gct cgg ctg cgg gaa atc ggg ctg aag cga ctg agt       144
ccg cga tgg aga aaa ctt tag aaa ctg ttc ctt tgg       180
aga gga aaa aga gag aaa agg aac agt tcc gta agc       216
tct tta ttg gtg gct taa gct ttg aaa cca cag aag       252
aaa gtt tga gga act act acg aac aat ggg gaa agc       288
tta cag act gtg tgg taa tga ggg atc ctg caa gca       324
aaa gat caa gag gat ttg gtt ttg taa ctt ttt cat       360
cca tgg ctg agg ttg atg ctg cca tgg ctg caa gac       396
ctc att caa ttg atg gga gag tag ttg agc caa aac       432
gtg ctg tag caa gag agg aat ctg gaa aac cag ggg       468
ctc atg taa ctg tga aga agc tgt ttg ttg gcg gaa       504
tta aag aag ata ctg agg aac atc acc tta gag att       540
act ttg agg aat atg gaa aaa ttg ata cca ttg aga       576
taa tta ctg ata ggc agt ctg gaa aga aaa gag gct       612
ttg gct ttg tta ctt ttg atg acc atg atc ctg tgg       648
ata aaa tcg tat tgc aga aat acc ata cca tca atg       684
gtc ata atg cag aag taa gaa agg ctt tgt cta gac       720
aag aaa tgc agg aag ttc aga gtt cta gga gtg gaa       756
gag gag gca act ttg gct ttg ggg att cac gtg gtg       792
gcg gtg gaa att tcg gac cag gac cag gaa gta act       828
tta gag gag gat ctg atg gat atg gca gtg gac gtg       864
gat ttg ggg atg gct ata atg ggt atg gag gag gac       900
ctg gag gtg gca att ttg gag gta gcc ccg gtt atg       936
gag gag gaa gag gag gat atg gtg gtg gag gac ctg       972
gat atg gca acc agg gtg ggg gct acg gag gtg gtt      1008
atg aca act atg gag gag gaa att atg gaa gtg gaa      1044
att aca atg att ttg gaa att ata acc agc aac ctt      1080
cta act acg gtc caa tga aga gtg aaa ctt tgt gtg      1116
gta gca gga aca tgg ggg gac cat atg gtg gag gaa      1152
act atg gtc cag gag gca gtg gag gaa gtg ggg gtt      1188
atg gtg gga gga gcc gat act gag ctt ctt cct att      1224
```

FIG. 3 Continued

```
tgc cat ggg ctt cac tgt ata aat agg aga gga tga        1260
gag ccc aga ggt aac aga aca gct tca ggt tat cga        1296
aat aac aat gtt aag gaa act ctt atc tca gtc atg        1332
cat aaa tat gca gtg ata tgg cag aag aca cca gag        1368
cag atg cag aga gcc att ttg tga atg gat tgg att        1404
att taa taa cat tac ctt act gtg gag gaa gga ttg        1440
taa aaa aaa atg cct ttg aga cag ttt ctt agc ttt        1476
tta att gtt gtt tct ttc tag tgg tct ttg taa gag        1512
tgt aga agc att cct tct ttg ata atg tta aat ttg        1548
taa gtt tca ggt gac atg tga aac ctt ttt taa gat        1584
ttt tct caa agt ttt gaa aag cta tta gcc agg atc        1620
atg gtg taa taa gac ata acg ttt ttc ctt taa aaa        1656
aat tta agt gcg tgt gta gag tta aga agc tgt tgt        1692
aca ttt atg att taa taa aat aat tct aaa gga aaa        1728
aaa aaa aaa aaa aaa aaa aaa aaa aaa aaa aa             1760
```

FIG. 4

```
  1   MExtletvplerkkREKEQFRKLFIGGLSFETTEESLRNYYEQWGKLTDCVVMRDPASKR
      •E---------REKEQFRKLFI                                 *         (4kDa)

61   SRGFGFVTFSSMAEVDAAMAARPHSIDGRVVEPKRAVAREESGKPGAHVTVKKLFVGGIK
                 *         •AARPHSIDGRVV                              (27,13kDa)

121   EDTEEHHLRDYFEEYGKIDTIEIITDRQSGKKRGFGFVTFDDHDPVDKIVLQKYHTINGH

181   NAEVRKALSRQEMQEVQSSRSGRGGNFGFGDSRGGGNFGPGPGSNFRGGSDGYGSGRGF
                       •QEVQSSRSGRGG                                  (15kDa)

241   GDGYNGYGGGPGGGNFGGSPGYGGGRRGGYGGGGPGYGNQGGGYGGGYDNYGGGNYGSGNY

301   NDFGNYNQQPSNYGPMKSGNFGGSRNMGGPYGGGNYGPGGSGGSGGYGGRSRY
                *                         *
```

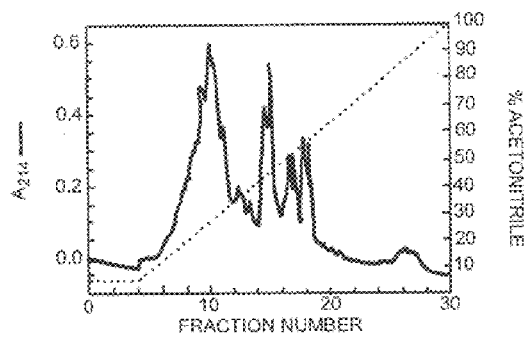
FIG. 5A
FIG. 5D
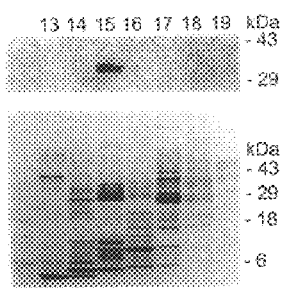
FIG. 5B
FIG. 5C
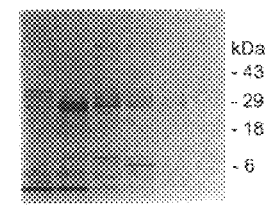
FIG. 5E
FIG. 5F

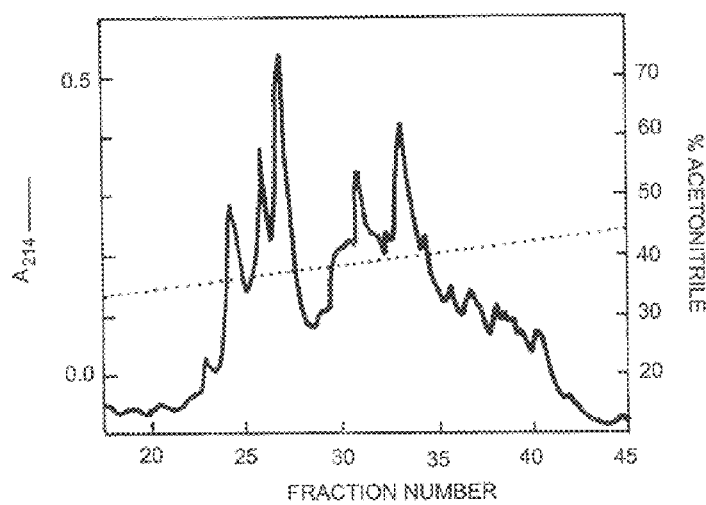
FIG. 6A
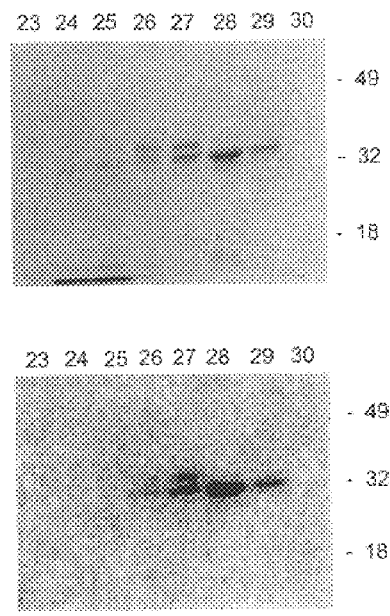
FIG. 6B
FIG. 6C

FIG. 7a

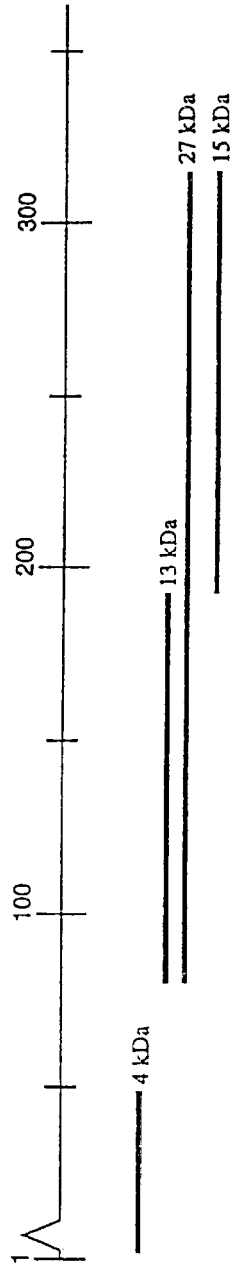

```
1    MEktletvpierkkREKEQFRKLFIGGLSFETTEESLRNYYEQWGKLTDCVVMRDPASKR
     •E----------REKEQFRKLFI (4 kDa)
                      *
61   SRGFGFVTFSMAEVDAAMAARPHSIDGRVVEPKRAVAREESGKPGAHVTVKKLFVGGIK
                   *  •AARPHSIDGRVV (13 kDa, 27 kDa)
121  EDTEEHHLRDYFEEYGKIDTIEIITDRQSGKKRGFGFVTFDDHDPVDKIVLQKYHTINGH
181  NAEVRKALSRQEMQEVQSSRSGRGGNFGFGDSRGGGNFGPGPGSNFRGGSDGYGSGRGF
          •QEVQSSRSGRGG (15 kDa)
241  GDGYNGYGGGPGGGNFGGSPGYGGGRGGYGGGPGYGNQGGGYGGGYDNYGGGNYGSGNY
301  NDFGNYNQQPSNYGPMKSGNFGGSRNMGGPYGGGNYGPGGSGGSGGYGGRSRY
                      *
```

FIG. 12A
FIG. 12B
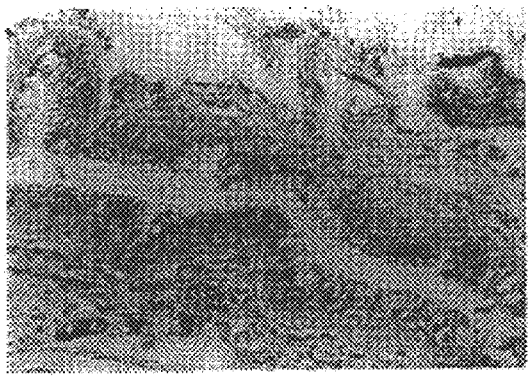
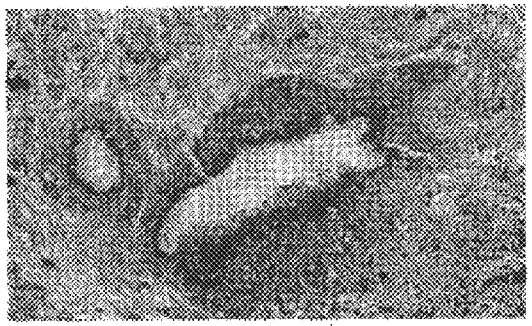
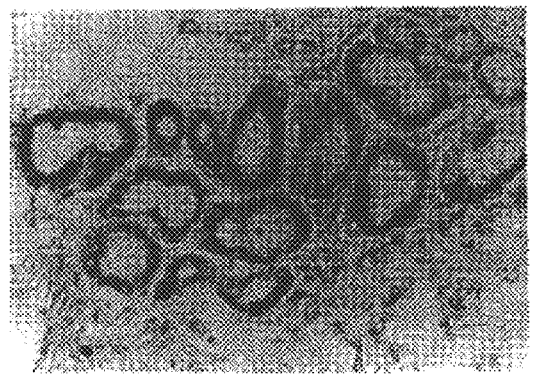
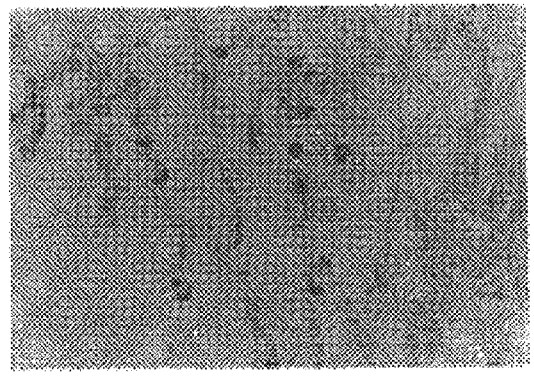
FIG. 12C
FIG. 12D

```
                          SEQUENCE LISTING (1) GENERAL INFORMATION:

(iii) NUMBER OF SEQUENCES:   23

(2) INFORMATION FOR SEQ ID NO: 1:

(i) SEQUENCE CHARACTERISTICS:
          (A) LENGTH:  12
          (B) TYPE:  Amino Acid
          (C) STRANDEDNESS:  Unknown
          (D) TOPOLOGY:  Linear (ii) MOLECULE TYPE: peptide (xi) SEQUENCE DESCRIPTION: SEQ ID NO: 1:

Ala Ala Arg Pro His Ser Ile Asp Gly Arg Val Val
 1               5                  10

(2) INFORMATION FOR SEQ ID NO: 2:

(i) SEQUENCE CHARACTERISTICS:
          (A) LENGTH:  12
          (B) TYPE:  Amino Acid
          (C) STRANDEDNESS:  Unknown
          (D) TOPOLOGY:  Linear (ii) MOLECULE TYPE: peptide (xi) SEQUENCE DESCRIPTION: SEQ ID NO: 2:

Gln Glu Val Gln Ser Ser Arg Ser Gly Arg Gly Gly
 1               5                  10

(2) INFORMATION FOR SEQ ID NO: 3:

(i) SEQUENCE CHARACTERISTICS:
          (A) LENGTH:  11
          (B) TYPE:  Amino Acid
          (C) STRANDEDNESS:  Unknown
          (D) TOPOLOGY:  Linear
```

(ii) MOLECULE TYPE: peptide (xi) SEQUENCE DESCRIPTION: SEQ ID NO: 3:

Arg Glu Lys Glu Gln Phe Arg Lys Leu Phe Ile
 1               5                  10

(2) INFORMATION FOR SEQ ID NO: 4:

(i) SEQUENCE CHARACTERISTICS:
           (A) LENGTH: 15
           (B) TYPE: Amino Acid
           (C) STRANDEDNESS: Unknown
           (D) TOPOLOGY: Linear (ii) MOLECULE TYPE: peptide (xi) SEQUENCE DESCRIPTION: SEQ ID NO: 4:

Glu Lys Thr Lys Glu Thr Val Pro Leu Glu Arg Lys
 1               5                  10

Lys Arg Glu
         15

(2) INFORMATION FOR SEQ ID NO: 5:

(i) SEQUENCE CHARACTERISTICS:
           (A) LENGTH: 10
           (B) TYPE: Amino Acid
           (C) STRANDEDNESS: Unknown
           (D) TOPOLOGY: Linear (ii) MOLECULE TYPE: peptide (xi) SEQUENCE DESCRIPTION: SEQ ID NO: 5:

Ala Ala Arg Pro Ser Asp Gly Arg Val Val
 1               5                  10

(2) INFORMATION FOR SEQ ID NO: 6:

(i) SEQUENCE CHARACTERISTICS:
           (A) LENGTH: 12
           (B) TYPE: Amino Acid
           (C) STRANDEDNESS: Unknown
           (D) TOPOLOGY: Linear (ii) MOLECULE TYPE: peptide (xi) SEQUENCE DESCRIPTION: SEQ ID NO: 6:

Glu Arg Glu Lys Glu Gln Phe Arg Lys Leu Phe Ile
 1               5                  10

(2) INFORMATION FOR SEQ ID NO: 7:

(i) SEQUENCE CHARACTERISTICS:
           (A) LENGTH: 353
           (B) TYPE: Amino Acid
           (C) STRANDEDNESS: Unknown
           (D) TOPOLOGY: Linear (ii) MOLECULE TYPE: peptide (xi) SEQUENCE DESCRIPTION: SEQ ID NO: 7:

Met Glu Lys Thr Leu Glu Thr Val Pro Leu Glu Arg
 1               5                  10

Lys Lys Arg Glu Lys Glu Gln Phe Arg Lys Leu Phe
            15                  20

Ile Gly Gly Leu Ser Phe Glu Thr Thr Glu Glu Ser

```
            25                  30                  35
Leu Arg Asn Tyr Tyr Glu Gln Trp Gly Lys Leu Thr
                40                  45
Asp Cys Val Val Met Arg Asp Pro Ala Ser Lys Arg
    50                  55                      60
Ser Arg Gly Phe Gly Phe Val Thr Phe Ser Ser Met
                65                  70
Ala Glu Val Asp Ala Ala Met Ala Ala Arg Pro His
        75                  80
Ser Ile Asp Gly Arg Val Val Glu Pro Lys Arg Ala
85                  90                  95
Val Ala Arg Glu Glu Ser Gly Lys Pro Gly Ala His
            100                 105
Val Thr Val Lys Lys Leu Phe Val Gly Gly Ile Lys
        110                 115                 120
Glu Asp Thr Glu Glu His His Leu Arg Asp Tyr Phe
                125                 130
Glu Glu Tyr Gly Lys Ile Asp Thr Ile Glu Ile Ile
            135                 140
Thr Asp Arg Gln Ser Gly Lys Lys Arg Gly Phe Gly
145                 150                 155
Phe Val Thr Phe Asp Asp His Asp Pro Val Asp Lys
                160                 165
Ile Val Leu Gln Lys Tyr His Thr Ile Asn Gly His
        170                 175                 180
Asn Ala Glu Val Arg Lys Ala Leu Ser Arg Gln Glu
                185                 190
Met Gln Glu Val Gln Ser Ser Arg Ser Gly Arg Gly
            195                 200
Gly Asn Phe Gly Phe Gly Asp Ser Arg Gly Gly Gly
205                 210                 215
Gly Asn Phe Gly Pro Gly Pro Gly Ser Asn Phe Arg
            220                 225
Gly Gly Ser Asp Gly Tyr Gly Ser Gly Arg Gly Phe
        230                 235                 240
Gly Asp Gly Tyr Asn Gly Tyr Gly Gly Gly Pro Gly
                245                 250
Gly Gly Asn Phe Gly Gly Ser Pro Gly Tyr Gly Gly
            255                 260
Gly Arg Gly Gly Tyr Gly Gly Gly Gly Pro Gly Tyr
265                 270                 275
Gly Asn Gln Gly Gly Gly Tyr Gly Gly Gly Tyr Asp
            280                 285
Asn Tyr Gly Gly Gly Asn Tyr Gly Ser Gly Asn Tyr
    290                 295                 300
Asn Asp Phe Gly Asn Tyr Asn Gln Gln Pro Ser Asn
                305                 310
Tyr Gly Pro Met Lys Ser Gly Asn Phe Gly Gly Ser
            315                 320
Arg Asn Met Gly Gly Pro Tyr Gly Gly Gly Asn Tyr
325                 330                 335
Gly Pro Gly Gly Ser Gly Gly Ser Gly Gly Tyr Gly
            340                 345
```

Gly Arg Ser Arg Tyr
    350

(2) INFORMATION FOR SEQ ID NO: 8:

(i) SEQUENCE CHARACTERISTICS:
        (A) LENGTH: 341
        (B) TYPE: Amino Acid
        (C) STRANDEDNESS: Unknown
        (D) TOPOLOGY: Linear (ii) MOLECULE TYPE: peptide (xi) SEQUENCE DESCRIPTION: SEQ ID NO: 8:

Met Glu Arg Glu Lys Glu Gln Phe Arg Lys Leu Phe
 1               5                  10

Ile Gly Gly Leu Ser Phe Glu Thr Thr Glu Ser
            15              20

Leu Arg Asn Tyr Tyr Glu Gln Trp Gly Lys Leu Thr
 25              30                  35

Asp Cys Val Val Met Arg Asp Pro Ala Ser Lys Arg
            40              45

Ser Arg Gly Phe Gly Phe Val Thr Phe Ser Ser Met
 50                  55                      60

Ala Glu Val Asp Ala Ala Met Ala Ala Arg Pro His
                65              70

Ser Ile Asp Gly Arg Val Val Glu Pro Lys Arg Ala
            75              80

Val Ala Arg Glu Glu Ser Gly Lys Pro Gly Ala His
 85                  90                      95

Val Thr Val Lys Lys Leu Phe Val Gly Gly Ile Lys
                100             105

Glu Asp Thr Glu Glu His His Leu Arg Asp Tyr Phe
            110             115                 120

Glu Glu Tyr Gly Lys Ile Asp Thr Ile Glu Ile Ile
                125             130

Thr Asp Arg Gln Ser Gly Lys Lys Arg Gly Phe Gly
            135             140

Phe Val Thr Phe Asp Asp His Asp Pro Val Asp Lys
145                 150                     155

Ile Val Leu Gln Lys Tyr His Thr Ile Asn Gly His
                160             165

Asn Ala Glu Val Arg Lys Ala Leu Ser Arg Gln Glu
    170             175                     180

Met Gln Glu Val Gln Ser Ser Arg Ser Gly Arg Gly
                185             190

Gly Asn Phe Gly Phe Gly Asp Ser Arg Gly Gly Gly
            195             200

Gly Asn Phe Gly Pro Gly Pro Gly Ser Asn Phe Arg
205                 210                     215

Gly Gly Ser Asp Gly Tyr Gly Ser Gly Arg Gly Phe
            220                 225

Gly Asp Gly Tyr Asn Gly Tyr Gly Gly Gly Pro Gly
        230                 235                 240

Gly Gly Asn Phe Gly Gly Ser Pro Gly Tyr Gly Gly
                245                 250

```
Gly Arg Gly Gly Tyr Gly Gly Gly Pro Gly Tyr
        255             260
Gly Asn Gln Gly Gly Tyr Gly Gly Gly Tyr Asp
265             270             275
Asn Tyr Gly Gly Gly Asn Tyr Gly Ser Gly Asn Tyr
            280             285
Asn Asp Phe Gly Asn Tyr Asn Gln Gln Pro Ser Asn
    290             295             300
Tyr Gly Pro Met Lys Ser Gly Asn Phe Gly Ser
            305             310
Arg Asn Met Gly Gly Pro Tyr Gly Gly Asn Tyr
        315             320
Gly Pro Gly Gly Ser Gly Gly Ser Gly Gly Tyr Gly
325             330             335
Gly Arg Ser Arg Tyr
            340

(2) INFORMATION FOR SEQ ID NO:9:

(i) SEQUENCE CHARACTERISTICS:
        (A) LENGTH: 769 base pairs
        (B) TYPE: nucleic acid
        (C) STRANDEDNESS: unknown
        (D) TOPOLOGY: linear (ii) MOLECULE TYPE: cDNA (xi) SEQUENCE DESCRIPTION: SEQ ID NO:9:
```

| | |
|---|---|
| ATGTCTAAGT CAGAGTCTCC TAAAGAGCCC GAACAGCTGA GGAAGCTCTT | 50 |
| CATTGGAGGG TTGAGCTTTG AAACAACTGA TGAGAGCCTG AGGAGCCATT | 100 |
| TTGAGCAATG GGGAACGCTC ACGGACTGTG TGGTAATGAG AGATCCAAAC | 150 |
| ACCAAGCGCT CTAGGGGCTT TGGGTTTGTC ACATATGCCA CTGTGGAGGA | 200 |
| GGTGGATGCA GCTATGAATG CAAGGCCACA CAAGGTGGAT GGAAGAGTTG | 250 |
| TGGAACCAAA GAGAGCTGTC TCCAGAGAAG ATTCTCAAAG ACCAGGTGCC | 300 |
| CACTTAACTG TGAAAAAGAT ATTTGTTGGT GGCATTAAAG AAGACACTGA | 350 |
| AGAACATCAC CTAAGAGATT ATTTTGAACA GTTTGGAAAA ATTGAAGTGA | 400 |
| TTGAAATCAT GACTGACCGA GGCAGTGGCA AGAAAAAGGG CTTTGCCTTT | 450 |
| GTAACCTTTG ACGACCATGA CTCCGTGGAT AAGATTGTCA TTCAGAAATA | 500 |
| CCATACTGTG AATGGCCACA ACTGTGAAGT TAGAAAAGCC CTGTCAAAGC | 550 |
| AAGAGATGGC TAGTGCTTCA TCCAGCCAAA GAGGTCGAAG TGGTTCTGGA | 600 |
| AACTTTGGTG GTGGTCGTGG AGGTGGTTTC GGTGGGAATG ACAACTTCGG | 650 |
| TCGTGGAGGA AACTTCAGTG GTCGTGGTGG CTTTGGTGGC AGCCGTGGTG | 700 |
| GTGGTGGATA TGGTGGCAGT GGGGATGGCT ATAATGGATT TGGCAATGAT | 750 |
| GGAAGCAATT TTGGAGGTG | 769 |

```
(2) INFORMATION FOR SEQ ID NO:10:

(i) SEQUENCE CHARACTERISTICS:
        (A) LENGTH: 764 base pairs
        (B) TYPE: nucleic acid
        (C) STRANDEDNESS: unknown
        (D) TOPOLOGY: linear
```

(ii) MOLECULE TYPE: cDNA (xi) SEQUENCE DESCRIPTION: SEQ ID NO:10:

| | | | | | |
|---|---|---|---|---|---|
| ATGGAGAGAG | AAAAGGAACA | GTTCCGTAAG | CTCTTTATTG | GTGGCTTAAG | 50 |
| CTTTGAAACC | ACAGAAGAAA | GTTTGAGGAA | CTACTACGAA | CAATGGGAA | 100 |
| AGCTTACAGA | CTGTGTGGTA | ATGAGGGATC | CTGCAAGCAA | AAGATCAAGA | 150 |
| GGATTTGGTT | TTGTAACTTT | TTCATCCATG | GCTGAGGTTG | ATGCTGCCAT | 200 |
| GGCTGCAAGA | CCTCATTCAA | TTGATGGGAG | AGTAGTTGAG | CCAAAACGTG | 250 |
| CTGTAGCAAG | AGAGGAATCT | GGAAAACCAG | GGGCTCATGT | AACTGTGAAG | 300 |
| AAGCTGTTTG | TTGGCGGAAT | TAAAGAAGAT | ACTGAGGAAC | ATCACCTTAG | 350 |
| AGATTACTTT | GAGGAATATG | GAAAAATTGA | TACCATTGAG | ATAATTACTG | 400 |
| ATAGGCAGTC | TGGAAAGAAA | AGAGGCTTTG | GCTTTGTTAC | TTTTGATGAC | 450 |
| CATGATCCTG | TGGATAAAAT | CGTATTGCAG | AAATACCATA | CCATCAATGG | 500 |
| TCATAATGCA | GAAGTAAGAA | AGGCTTTGTC | TAGACAAGAA | ATGCAGGAAG | 550 |
| TTCAGAGTTC | TAGGAGTGGA | AGAGGAGGCA | ACTTTGGCTT | TGGGGATTCA | 600 |
| CGTGGTGGCG | GTGGAAATTT | CGGACCAGGA | CCAGGAAGTA | ACTTTAGAGG | 650 |
| AGGATCTGAT | GGATATGGCA | GTGGACGTGG | ATTTGGGGAT | GGCTATAATG | 700 |
| GGTATGGAGG | AGGACCTGGA | GGTGGCAATT | TTGGAGGTAG | CCCCGGTTAT | 750 |
| GGAGGAGGAA | GAGG | | | | 764 |

(2) INFORMATION FOR SEQ ID NO: 11:

(i) SEQUENCE CHARACTERISTICS:
      (A) LENGTH: 20
      (B) TYPE: nucleic acid
      (C) STRANDEDNESS: Unknown
      (D) TOPOLOGY: Linear (ii) MOLECULE TYPE: other nucleic acid (xi) SEQUENCE DESCRIPTION: SEQ ID NO: 11:

GAGTCCGGTT CGTGTTCGTC                              20

(2) INFORMATION FOR SEQ ID NO: 12:

(i) SEQUENCE CHARACTERISTICS:
      (A) LENGTH: 23
      (B) TYPE: nucleic acid
      (C) STRANDEDNESS: Unknown
      (D) TOPOLOGY: Linear (ii) MOLECULE TYPE: other nucleic acid (xi) SEQUENCE DESCRIPTION: SEQ ID NO: 12:

TGGGCTCTCA TCCTCTCCTA TTA                          23

(2) INFORMATION FOR SEQ ID NO: 13:

(i) SEQUENCE CHARACTERISTICS:
      (A) LENGTH: 19
      (B) TYPE: nucleic acid
      (C) STRANDEDNESS: Unknown
      (D) TOPOLOGY: Linear (ii) MOLECULE TYPE: other nucleic acid (xi) SEQUENCE DESCRIPTION: SEQ ID NO: 13:

```
CTACAGCGCC AGGACGAGT                                                      19
```

(2) INFORMATION FOR SEQ ID NO: 14:

(i) SEQUENCE CHARACTERISTICS:
        (A) LENGTH: 19
        (B) TYPE: nucleic acid
        (C) STRANDEDNESS: Unknown
        (D) TOPOLOGY: Linear (ii) MOLECULE TYPE: other nucleic acid (xi) SEQUENCE DESCRIPTION: SEQ ID NO: 14:

```
CCCATGGCAA TAGGAACAA                                                      19
```

(2) INFORMATION FOR SEQ ID NO: 15:

(i) SEQUENCE CHARACTERISTICS:
        (A) LENGTH: 24
        (B) TYPE: nucleic acid
        (C) STRANDEDNESS: Unknown
        (D) TOPOLOGY: Linear (ii) MOLECULE TYPE: other nucleic acid (xi) SEQUENCE DESCRIPTION: SEQ ID NO: 15:

```
TGTTCTGTTA CCTCTGGGCT CTCA                                                24
```

(2) INFORMATION FOR SEQ ID NO: 16:

(i) SEQUENCE CHARACTERISTICS:
        (A) LENGTH: 29
        (B) TYPE: Amino Acid
        (C) STRANDEDNESS: Unknown
        (D) TOPOLOGY: Linear (ii) MOLECULE TYPE: peptide (xi) SEQUENCE DESCRIPTION: SEQ ID NO: 16:

```
Ala Thr Val Glu Glu Val Asp Ala Ala Met Asn Ala
 1               5                  10

Arg Pro His Lys Val Asp Gly Arg Val Val Glu Pro
            15                  20

Lys Arg Ala Val Ser
25
```

(2) INFORMATION FOR SEQ ID NO: 17:

(i) SEQUENCE CHARACTERISTICS:
        (A) LENGTH: 29
        (B) TYPE: Amino Acid
        (C) STRANDEDNESS: Unknown
        (D) TOPOLOGY: Linear (ii) MOLECULE TYPE: peptide (xi) SEQUENCE DESCRIPTION: SEQ ID NO: 17:

```
Asp Asp His Asp Ser Val Asp Lys Ile Val Ile Gln
 1               5                  10

Lys Tyr His Thr Val Asn Gly His Asn Cys Glu Val
            15                  20

Arg Lys Ala Leu Ser
25
```

(2) INFORMATION FOR SEQ ID NO: 18:

```
    (i) SEQUENCE CHARACTERISTICS:
        (A) LENGTH: 19
        (B) TYPE: nucleic acid
        (C) STRANDEDNESS: Unknown
        (D) TOPOLOGY: Linear (ii) MOLECULE TYPE: other nucleic acid (xi) SEQUENCE DESCRIPTION: SEQ ID NO: 18:

TGGCAGCATC AACCTCAGC                                              19

(2) INFORMATION FOR SEQ ID NO: 19:

(i) SEQUENCE CHARACTERISTICS:
        (A) LENGTH: 22
        (B) TYPE: nucleic acid
        (C) STRANDEDNESS: Unknown
        (D) TOPOLOGY: Linear (ii) MOLECULE TYPE: other nucleic acid (iv) ANTI-SENSE: YES (xi) SEQUENCE DESCRIPTION: SEQ ID NO: 19:

GAGAGAGAAA AGGAACAGTT CC                                          22

(2) INFORMATION FOR SEQ ID NO: 20:

(i) SEQUENCE CHARACTERISTICS:
        (A) LENGTH: 24
        (B) TYPE: nucleic acid
        (C) STRANDEDNESS: Unknown
        (D) TOPOLOGY: Linear (ii) MOLECULE TYPE: other nucleic acid (iv) ANTI-SENSE: YES (xi) SEQUENCE DESCRIPTION: SEQ ID NO: 20:

TAAGCTTTCC CCATTGTTCG TAGT                                        24

(2) INFORMATION FOR SEQ ID NO: 21:

(i) SEQUENCE CHARACTERISTICS:
        (A) LENGTH: 19
        (B) TYPE: nucleic acid
        (C) STRANDEDNESS: Unknown
        (D) TOPOLOGY: Linear (ii) MOLECULE TYPE: Nucleic Acid (iv) ANTI-SENSE: NO (xi) SEQUENCE DESCRIPTION: SEQ ID NO: 21:

CTACAGCGCC AGGACGAGT                                              19

(2) INFORMATION FOR SEQ ID NO: 22:

(i) SEQUENCE CHARACTERISTICS:
        (A) LENGTH: 20
        (B) TYPE: nucleic acid
        (C) STRANDEDNESS: Unknown
        (D) TOPOLOGY: Linear (ii) MOLECULE TYPE: other nucleic acid (iv) ANTI-SENSE: YES (xi) SEQUENCE DESCRIPTION: SEQ ID NO: 22:

CCCATGGCAA ATAGGAAGAA                                             20
```

(2) INFORMATION FOR SEQ ID NO: 23:

(i) SEQUENCE CHARACTERISTICS:
        (A) LENGTH: 18
        (B) TYPE: nucleic acid
        (C) STRANDEDNESS: Unknown
        (D) TOPOLOGY: Linear (ii) MOLECULE TYPE: other nucleic acid (iv) ANTI-SENSE: NO (xi) SEQUENCE DESCRIPTION: SEQ ID NO: 23:

```
GCTCGGCTGC GGGAAATC                                              18
```

METHODS FOR DIAGNOSING CANCER OR PRECANCER BASED UPON HNRNP PROTEIN EXPRESSION

CROSS REFERENCE TO RELATED APPLICATIONS

This application is a continuation of U.S. patent application Ser. No. 09/255,609, which was filed on Feb. 19, 1999, which is a divisional of U.S. patent application Ser. No. 08/538,711, which was filed on Oct. 02, 1995 and issued as U.S. Pat. No. 5,994,062 on Nov. 30, 1999. The disclosures of all of the aforementioned applications are incorporated herein by reference.

FIELD OF THE INVENTION

The present invention relates to the area of cancer diagnostics and therapeutics. More specifically, the invention relates to the isolation and purification of an early cancer detection marker protein of epithelial cells and the cloning of the DNA sequence encoding the protein. The invention further relates to the protein and DNA sequence for detecting and diagnosing individuals predisposed to cancer. The present invention also relates to therapeutic intervention to regulate the expression of the gene product.

BACKGROUND OF THE INVENTION

Lung cancer is the most frequent cause of cancer death of both males and females in the United States, accounting for one in three cancer deaths[1]. In the last thirty years, cancer-related survival of this disease has improved only minimally. Successful treatment of this disease by surgical resection and drug chemotherapy is strongly dependent on identification of early-stage tumors. A conceptually attractive early detection approach is to establish the presence of a cancer by evaluation of shed bronchial epithelial cells. In the late 1960's Saccomanno et al. proposed the use of sputum cytology to evaluate cytomorphologic changes in the exfoliated bronchial epithelium as a technique to enhance the early detection of lung cancer[2]. However, clinical trials using combination chest X-ray and sputum cytology have not shown any decrease in cancer-related mortality[3].

In 1988, Tockman et al. reported a sensitive method for early lung cancer detection by immunostaining cells contained within sputum samples with two lung cancer-associated monoclonal antibodies[4]. The basis for this approach was to identify early pre-neoplastic changes in cells shed from bronchial epithelium. The antibodies used in that study were mouse monoclonal IgG's designated 703D4, disclosed in U.S. Pat. No. 4,569,788, and 624H12. In an analysis of the contribution of the individual monoclonal antibodies to early detection of lung cancer, 703D4 alone identified 20 of the 21 detected true positive cases (4; U.S. Ser. No. 08/152,881 which issued to U.S. Pat. No. 5,455,159 on Oct. 3, 1995). 624H12 has been shown to detect an oncofetal antigen which is the Lewis'-related portion of a cell-surface glycoprotein (Mulshine/Magnani). The antigen for 703D4 was unknown.

703D4 was developed by immunization using a whole tumor cell extract, coupled to keyhole limpet hemocyanin, and selection was based on discrimination amongst subtypes of lung cancer histological subtypes. Preliminary studies showed the 703D4 antibody recognized a protein expressed by most non-small cell lung cancer cells[5]. Immunoprecipitation defined a protein of Mr>31 kDa. Since 703D4 demonstrated the ability to selectively detect changes related to the development of cancer in shed bronchial epithelium from the proximal airways, the antigen recognized by 703D4 was purified in the present invention to determine its identity and explore its relationship to early lung cancer detection. The present invention uses a biochemical approach for identification of the epithelial protein from non-small cell lung tumor cells.

With cigarette smoking the entire human respiratory tract is exposed to potential carcinogens and is at increased risk for cancer development. This phenomenon has been called "field cancerization" (8). A variety of epithelial changes have been observed throughout the respiratory tract of both smokers and lung cancer patients (8,9), which may be part of the "field" effect. Saccomanno et al. (6) have demonstrated that centrally located squamous carcinomas of the lung develop through a series of identifiable stages, namely squamous metaplasia, squamous metaplasia with atypia (mild, moderate, marked), carcinoma in situ, and invasive carcinoma (6). These findings were confirmed by later animal and human studies (7). This cytomorphologic classification is useful in defining preneoplastic changes in the proximal region of the lung cancer "field". However, comparable events preceding the other major lung cancer histologies, especially those arising in the peripheral lung (terminal and respiratory bronchioles, alveolar epithelium) are not well defined.

The expression of an epithelial protein in both neoplastic and nonneoplastic regions of distal human lung was investigated.

SUMMARY OF THE INVENTION

The present invention describes the isolation and identification of an epithelial protein which is an early marker for cancer. It is an object of the present invention to provide an isolated and purified epithelial protein, peptide, or variants thereof which are an early marker for lung cancer.

It is an object of the present invention to provide an isolated, purified DNA molecule or portion thereof comprising the coding sequence for an epithelial protein, peptide or variant thereof which is an early marker for cancer.

It is another object of the invention to utilize the isolated DNA, or RNA molecule or portion thereof encoding the epithelial protein which is an early marker for cancer to detect and diagnose the gene and alterations thereof in tissues and cells.

It is another object of the invention to provide nucleic acid probes for the detection of the gene or protein thereof encoding an epithelial protein which is an early marker for cancer.

It is still another object of the invention to provide a method for diagnosing human preneoplastic and neoplastic cells and tissues. In accordance with the invention, the method comprises isolating cells, tissues or extracts thereof from a human and detecting the gene or portion thereof encoding an epithelial protein which is an early marker for cancer or their expression products from the cells, tissue or extracts thereof, wherein detection of a quantitative increase in the gene or expression products indicates preneoplasia and neoplasia.

Another object of the invention is a method for detecting mutations of a gene encoding the epithelial protein which is an early marker for cancer, contained within clones expressing the gene recovered from cancer cell.

Another method for diagnosing human preneoplastic and neoplastic cells and tissues is by detecting post-translational modifications of the epithelial protein in the preneoplastic and neoplastic cells and tissue by immunoassays such as Western blot or immunoelectrophoresis using an antibody that is reactive with the epithelial protein, by two-dimensional electrophoresis or by reverse-phase HPLC.

It is yet another object of the invention to provide a method for monitoring the efficacy of a therapeutic intervention to arrest cancer progression.

It is a further object of the invention to provide a kit comprising oligonucleotides comprising a nucleic acid sequence from DNA, RNA or portion thereof encoding the epithelial protein which is an early marker for cancer, for use in the methods of diagnosis of cancer and early cancer and for use in methods of monitoring the efficacy of cancer treatment.

Still another object of the invention is to provide the epithelial protein, peptides or variants thereof which one substantially homologous to a portion of at least one heterogenous nuclear ribonucleotide protein for use in diagnostic and detection assays, in particular for immunoassays.

One object of the invention is an inhibitory protein analog of the epithelial protein which is capable of binding to the same binding site recognized by the epithelial protein on RNA. Such an analog is capable of competitively inhibiting the function of the epithelial protein, peptide or variant thereof in vitro and in vivo.

It is yet another object of the invention to provide a method for detecting susceptibility to cancer and for diagnosing early-onset tumorigenesis in mammalian cells and tissue. In accordance with the invention, the method comprises isolating a mammalian biological sample and detecting a nucleic acid sequence encoding an epithelial protein or portion thereof which is an early marker for cancer.

Yet another object of the invention is to provide a method of altering or downregulating the expression of the gene or portion thereof encoding an epithelial protein or portion thereof which is an early marker for cancer of epithelial cells which comprises introduction of antisense oligonucleotides which are substantially complementary to the gene in the epithelial cell. The antisense oligonucleotide allows for non-neoplastic growth of the epithelial cell.

Another object of the invention is to provide a method for screening for chemotherapeutic drugs and for monitoring the efficacy of a chemotherapeutic and intervention drugs.

It is a further object of the invention to provide a transgenic animal which has incorporated into its genome one or more copies of a nucleic acid sequence which encodes an epithelial protein which is an early marker for cancer. The incorporation of the nucleic acid sequence results in overexpression or expression of multiple forms or variants of the epithelial protein. The resulting transgenic animal is more prone to develop cancer and may develop cancer at an accelerated rate at one or more locations in the body. Such transgenic animals are useful for screening therapeutic drugs useful for treating or inhibiting cancer.

It is yet another object of the invention to provide an antibody reactive to an epithelial protein, peptide or variant thereof. Such antibodies are useful in diagnosis and treatment of cancer.

BRIEF DESCRIPTION OF DRAWINGS

These and other objects, features, and many of the advantages of the invention will be better understood upon a reading of the following detailed description when considered in connection with the accompanying drawings wherein:

FIG. 1 shows the DNA coding sequence of heterogenous ribonucleoprotein A1 (hnRNP) and hnRNP A2.

FIG. 2 shows the full DNA sequence of human hnRNPA2 disclosed by Burd, C. G. et al *Proc. Nat'l Acad. Sci. USA* 86, 9788–9792 (1989).

FIG. 3 shows the full DNA sequence of human hnRNPB1 disclosed by Burd, C. G. et al *Proc. Nat'l Acad. Sci. USA* 86:9788–9792 (1989).

FIG. 4 shows the amino acid sequence of peptides sequenced from CNBr digest of purified 703D4 antigen, aligned with hnRNP-A2/B1. Alignment of CNBr-generated fragments of purified 703D4 antigen with predicted sequence of the hnRNP-A2/B1 (numbering for hnRNP-B1). Lower case letters (amino acids 3-14) denote the alternately-spliced exon missing in hnRNP-A2. Methionines subject to CNBr cleavage are denoted by ● or *. Peptides commencing after a * methionine would be too small for visualization by Tricine SDS-PAGE (<2 kDa). Identical data were obtained from three separate purifications of 703D4 antigen. In each case two bands yielded the sequence AARPHSIDGRVV, and several variable minor bands were seen, suggesting partial CNBr cleavage possibly due to oxidized methionines.

FIGS. 5a through 5e show polymeric reversed phase HPLC purification of 703D4 antigen. 10mm×10 cm Poros perfusion polymeric $C_{18}$ column was equilibrated with 5% acetonitrile/0.1% TFA (5a) and 5% methanol0.1% HFBA (5d). Protein was eluted with a gradient of 5–100% acetonitrile (5A) and 5–100% methanol (5d) at a flow rate of 10 ml/min. Fractions were run on two identical SDS-PAGE gels and one stained with Coomassie blue (5c, 5f), the other transferred to PVDF for reaction with 703D4 antibody (5b, 5e). Positions of protein standards are shown on the right (43, 29, 18 and 6 kDa). In the a panels, note the separation of ampholytes, urea and the major protein from the protein of insterest (fraction 15, 16 in 5b and fraction 34, 35 in 5e). Immunoreactivity positive fractions were pooled for additonal purification.

FIGS. 6a through 6c show $C_4$ reversed phase HPLC purification of 703D4 antigen. 6a, c4 column, eluted with a gradient of 33–48% acetonitrile in 0.1% TFA. 6b and 6c shown Western blot and Coomassie blue analysis of eluted fractions, respectively (49, 32 and 18 kDa protein standards are on the right).

FIG. 7a shows the amino acid alignment of the peptides of the present invention with heterogeneous nuclear ribonucleoprotein B2 (hnRNP-A2 is denoted by Λ skipped area) ●, * methionines; * peptides produced by CNBr at this Met too small for Tricine SDS-PAGE.

FIGS. 12A through 12D shows P31 expression pattern in non-neoplastic lung (lacking histologic abnormalities). 12A) Diffuse granular localization of p31 towards the apical portion of ciliated and non-ciliated bronchial epithelium. Note faint staining of underlying basal cells (arrows) (Immunohistochemical staining, X225). 12B) Strong p31 expression in bronchial glands (Immunoperoxidase, X225). 12C) p31 expression in bronchial (Immunohistochemical staining, X270). 12D) Localization of p31 in normal type II cells. Note moderate staining intensify and the distribution of normal type II cells along alveolar delicate (normal) septa. (Immunoperoxidase, X360).

FIGS. 13A through 13B show variable localization of p31 expression in type II cell hyperplasia. 8A) Type II hyperplasia demonstrating strong diffuse cytoplasmic p31 immunoreactivity. Note increased number of type II cells and presence of fibrosis as compared with normal alveolar epithelium in FIG. 12D (Immunohistochemical of p31 in type II cell hyperplasia. (Immunohistochemical staining, X360). 13B shows membranous pattern of positive expression with Type II pneumocytes.

DETAILED DESCRIPTION OF THE INVENTION

Figure 7B:
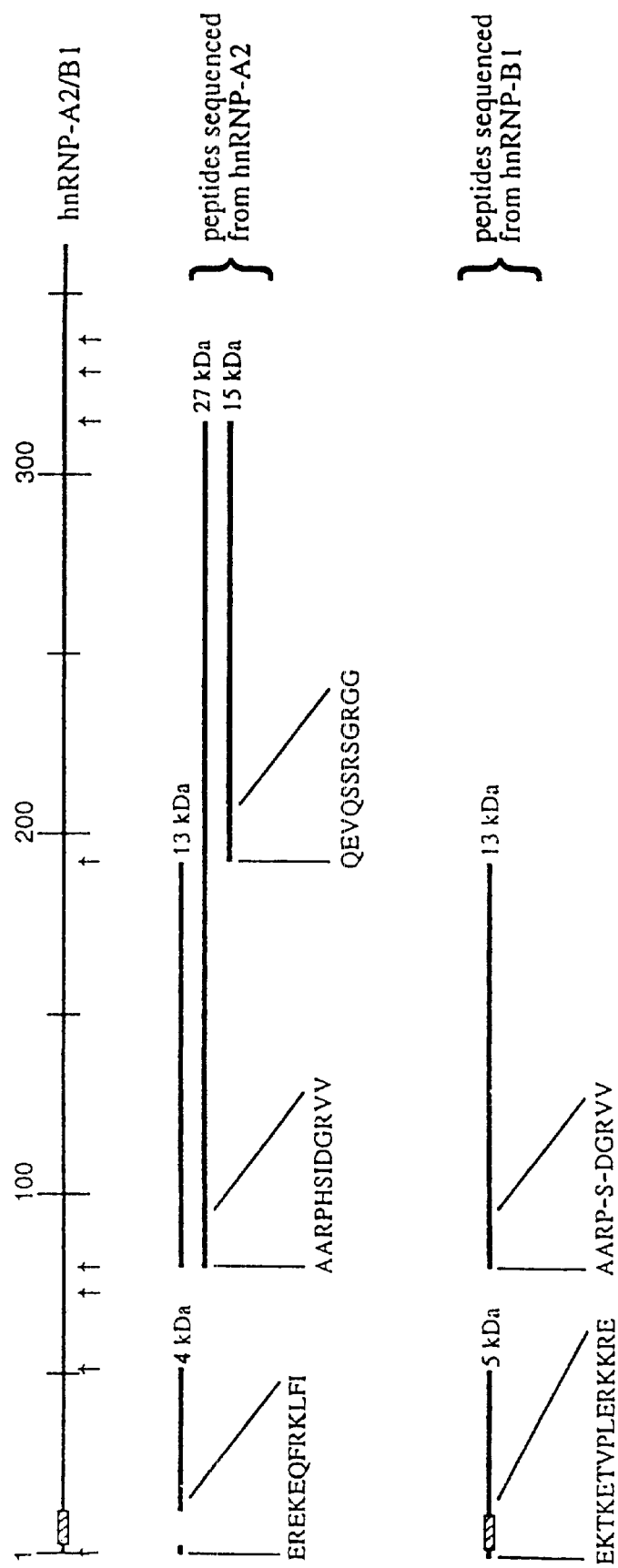
FIG. 7b shows the N-terminal amino acid sequences and approximate Mr of CNBr cleavage fragments of the purified 703D4 major (hnRNP-A2) and minor (hn-RNP-B1) antigens. Arrows indicate the positions of methionines within the protein, and the carrot indicates the site of alternately spliced exon differentiating hnRNP-A2 from B1. The exact methionine at which the 15 kDa and 27 kDa peptides terminates could not be determined from the SDS-PAGE analysis. All peptides which were not recovered are too small to be resolved from the migration front of the Tricine SDS-PAGE gel (<2.5 kDa).

The present invention is an isolated and purified protein, peptide and derivatives thereof as well as variants thereof which is an early detection marker for cancer. The protein, peptides and variants thereof are characteristically present in low levels from normal cells and are present in high levels from pre-cancer and most cancer cells. As used herein, variants include altered proteins that arise from DNA mutations, alternate exon splicing and post translational modifications. Expression of such variant proteins correlates with transformation of normal cells to a precancer or cancer cell.

Of particular interest is a protein having a molecular weight of about 31 KDa to about 35 KDa and peptides and variants thereof isolated and purified from pre-neoplastic and neoplastic cells of the lung, colon, kidney, bone, breast, prostate, melanoma, myeloma and the like. The protein and peptides and variants thereof of the present invention are markers for epithelial cells which are committed to a pathway of transformation leading to development of lung cancer. A preferred protein and variant thereof is isolated from human lung cancer cells, in particular, non-small cell cancer cells.

The isolated and purified protein and variants thereof of the present invention comprises at least one of the following amino acid sequences, preferably more than one of the sequences:

```
AARPHSIDGRVV        (SEQ ID. NO.: 1);
QEVQSSRSGRGG        (SEQ ID. NO.: 2);
REKEQFRKLFI         (SEQ ID. NO.: 3);
EKTKETVPLERKKRE     (SEQ ID. NO.: 4);
AARPSDGRVV          (SEQ ID. NO.: 5);
EREKEQFRKLFI        (SEQ ID. NO.: 6).
```

In one embodiment, the protein, peptide and variants thereof are characterized by a molecular weight of about 4 kDa and comprise the amino acid sequence according to sequence I.D. No.: 3. In another embodiment the protein, peptide and variants thereof are characterized by a molecular weight of about 27 kDa and comprises the amino acid sequence according to sequence I.D. No.: 1. In yet another embodiment the protein, peptide and variants thereof are characterized by a molecular weight of about 13 kDa and comprises the amino acid sequence according to sequence I.D. No.: 1. In still another embodiment of the invention the protein, peptide and variants thereof are characterized by a molecular weight of 15 kDa and comprises amino acid sequence I.D. No.: 2.

In one embodiment, the protein, peptides and variants thereof, share partial amino acid sequence homology with at least one or more heterogenous nuclear ribonucleotide proteins (hn-RNP). The protein peptides and variants of the present invention may share partial amino acid sequence homology with one or more of the hn-RNP selected from the group consisting of hn-RNPA1, hn-RNPA2, hn-RNP-B1, hn-RNPB2, hn-RNPC1, hn-RNPC2 and hn-RNPC3. In a particular embodiment, the protein shares partial amino acid sequence homology with hn-RNP A2. In another embodiment, the protein shares partial amino acid sequence homology with hn-RNP B1. In a preferred embodiment of the present invention, the protein shares partial amino acid sequence homology with hn-RNP A2 and hn-RNP B1. By partial amino acid sequence homology is meant a protein, peptide or variant thereof having at least 70% sequence homology with at least one hn-RNP, preferably at least about 90% sequence homology, more preferably at least about 95% sequence homology with at least one or more hn-RNP.

In one embodiment the protein, peptide or variant shares sequence homology with the following amino acid sequence or portion thereof:

```
  1 MEktletvplerkkREKEQFRKLFIGGLSFETTEESLRNYYEQWGKLTDCVVMRDPASKR(SEQ ID NO. 7)

61 SRGFGFVTFSSMAEVDAAMAARPHSIDGRVVEPKRAVAREESGKPGAHVTVKKLFVGGIK

121 EDTEEHHLRDYFEEYGKIDTIEITTDRQSGKKRGFGFVTFDDHDPVDKIVLQKYHTINGH

181 NAEVRKALSRQEMQEVQSSRSGRGGNFGFGDSRGGGNFGPGPGSNFRGGSDGYGSGRGF

241 GDGYNGYGGGPGGGNFGGSPGYGGGRGGYGGGGPGYGNQGGGYGGGYDNYGGGNYGSGNY

301 NDFGNYNQQPSNYGPMKSGNFGGSRNMGGPYGGGNYGPGGSGGSGGYGGRSRY
```

In another embodiment, the protein peptide or variant thereof shares sequence homology with the following amino acid sequence or portion thereof:

```
  1 MEREKEQFRKLFIGGLSFETTEESLRNYYEQWGKLTDCVVMRDPASKR            (SEQ ID NO. 8)

61 SRGFGFVTFSSMAEVDAAMAARPHSIDGRVVEPKRAVAREESGKPGAHVTVKKLFVGGIK

121 KDTEEHHLRDYFEEYGKIDTIEITTDRQSGKKRGFGFVTFDDHDPVDKIVLQKYHTINGH

181 NAEVRKALSRQEMQQEVQSSRSGRGGNF-
    GFGDSRGGGNFGPGPGSNFRGGSDGYGSGRGF

241 GDGYNGYGGGPGGGNFGGSPGYGGGRGGYGGGGPGYGNQGGGYGGGYDNYGGGNYGSGNY

301 NDFGNYNQQPSNYGPMKSGNFGGSRNMGGPYGGGNYGPGGSGGSGGYGGRSRY
```

Variants include but are not limited to proteins and peptides that vary in amino acid sequence by one or more than one amino acid, preferably do not vary by more than 10 amino acids, preferably not more than 5 amino acids, more preferably not more than 1–3 amino acids. The amino acid change may be conservative substitutions, deletions and the like. Examples of these amino acid changes include but are not limited to alteration of aromatic amino acid to alter DNA/RNA binding sites; methylation of arginine, lysine or histidine including $N^G$, $N^G$-dimethyl-arginine near the COOH terminus; phosphoserines or phosphothreonine, blocked N-terminus glycosylation, and the like. Variants also encompass alternate mRNA splice forms of the protein or peptides.

Also included as variants are proteins and peptides having one or more post-translational modifications of amino acids. Examples of post-translational modifications include but are not limited to glycosylation, phosphorylation, methylation, ADP ribosylation and the like. In one embodiment, the variant has a post-translational modification of a methylation on the N-terminal amino acid or phosphorylations of serines and threonines. In another embodiment, the variant has a post-translational modification of C-terminal glycines for affecting protein binding.

Also encompassed by the term variant, are derivatives of the proteins, peptides and post-translational modified proteins and peptides that may have other constituents attached thereto such as radiolabels, biotin, fluorescein and chemiluminescent labels and the like.

Inhibitory protein or peptide analogs are also encompassed in the invention. Such inhibitory protein or peptide analogs are capable of competitively inhibiting the binding of the epithelial protein to its binding site on RNA.

The identification of the 703D4 early lung cancer detection antigen as sharing amino acid sequence homology with hnRNP A2/B1 is provocative in light of the emerging knowledge about the hnRNP group of proteins (Burd and Dreyfuss, Science, Vol. 265 (July 29) pp. 615–621, 1994).

The family of hnRNP have roles in RNA processing, including pre-mRNA exon splicing and splice site choice, and also in transcription, DNA replication, and recombination (reviewed in Dreyfuss et al., Ann Rev Biochem., Vol. 62, pp 289–321, year 1993. Some hnRNPs are involved in shuttling mRNA from the nucleus to the cytosol, which is consistent with both our immunohistochemical localization reported previously and subcellular fractionation. A variety of post-translational modifications have been reported for members of the hnRNP family.

Post-translational modifications of the epithelial protein, peptide or variants thereof of the present invention are identified by methods known in the art such as two dimensional electrophoresis, reverse-phase APLC (Karn, J. et al J. Biol. Chem. 252, No. 20, pp 7307–7322, 1977; Anderson, N. L. Electrophroesis 12, pp. 907–930, 1991; Boffa, L. C. et al. Biochemical and Biophys. Res. Commun., 74, No. 3, 1977; Williams, K. R. et al. Proc. Natl. Acad. Sci USA, vol. 82, pp. 5666–5670, 1985; Kumar, A. et al. J. Biol. Chem., vol. 261, No. 24, pp. 11266–11273, 1986; Medzihradsky, K. F. et al. Am. Soc. Mass. Spectrom, vol. 5, pp. 350–358, 1994). One method uses two dimensional gels analysis. A purified epithelial protein peptide or variant with and without enzymatic treatment is electrophoresed in the first dimension. The second dimension is conducted under a pH gradient of about pH 8 to about 9.5 (Anderson Electrophoresis 12:907, 1991). The protein peptide or variant may be detected by methods known in the art such as protein staining, radiolabelled metabolic labels, antibody and the like. The shift in migration pattern is indicative of a post-translation modification.

Post-translational modifications are also determined using specific enzymes such as phosphatase, glucosidase and the like to treat samples separated by two dimensional gel electrophoresis or by electrospray API-mass spectroscopy (Medzihradsky, Am. Soc. Mass. Spec., 5:350, 1994) and the molecular weight of the treated samples compared with non-treated samples.

Figure 10:
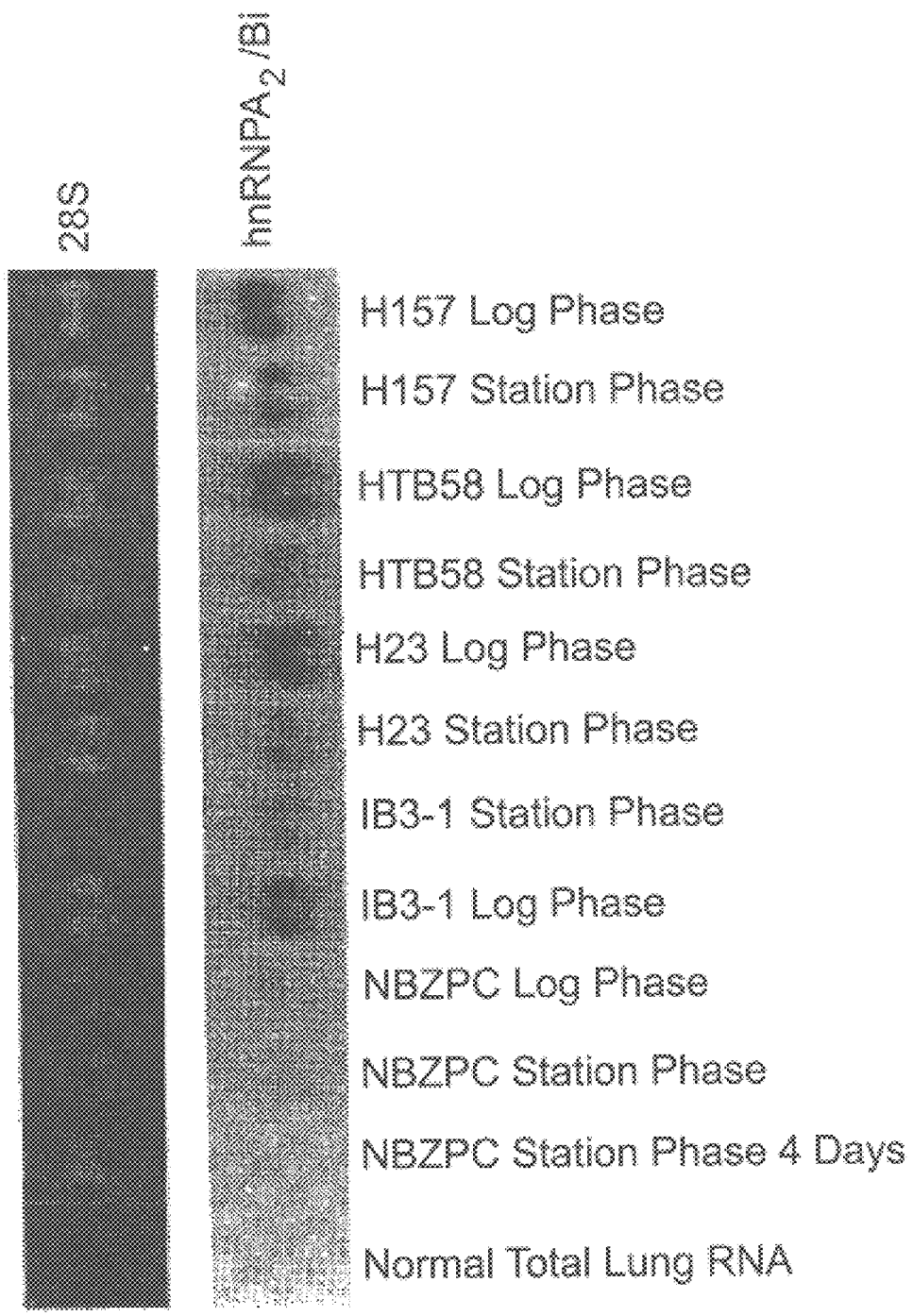
FIG. 10 shows proliferation-dependent control of hnRNP-A2/B1 expression. Northern blot hybridization with probes specific for hnRNP A2/B1 to 10 μg of total RNA from NSCLC (H157, HTB58 H23); a transformed bronchial epithelium cell line (IB3-1) and normal bronchial epthelium primary culture (NBEPC) log phase and station phase. Quantification of the loaded RNA was obtained by ethidium bromide staining of 28s rRNA (EtBr).

In one embodiment, the invention demonstrates deregulation and overexpression of the an early lung cancer epithelial protein in cancer cell lines and in transformed bronchial epithelial cells compared to short term, normal primary bronchial epithelial cultures. This data parallel previous work on the closely related molecule hnRNP-A1 which showed deregulation of expression in transformed cells including fibroblast cells (Biamonti, *J. Mol. Biol.*, Vol. 230, pp 77–89, 1993). In transformed cell lines including tumor cell lines, high level of hnRNP-A1 expression is maintained in cultures which have reached stationary phase, whereas normal primary fibroblast cultures express hnRNP-A1 only during the logarithmic phase of cell growth (FIG. 10).

The protein and variants thereof may be isolated from natural sources or may be chemically synthesized or recombinantly produced by techniques known in the art. Technique for chemical synthesis are described in J.M. Steward and J. D. Young, "Solid Phase Peptide Synthesis", W. H. Freeman & Co., San Francisco, 1969; M. Bodansky, et al. "Peptide Synthesis", John Wiley & Sons, Second Edition, 1976 and J. Meienhofer, "Hormonal Proteins and Peptides" Vol. 2, p.46, Academic Press, New York, 1983 and E. Schroder and K. Kubké, "The Peptides", Vol. 1, Academic Press, New York, 1965.

The protein, peptides and variant thereof is at least about 90% pure, preferably at least about 95% pure, more preferably greater than 95% pure.

The present invention also encompasses compositions comprising the epithelial protein, peptides, and variants thereof which are early markers for precancer and cancer each as separate molecular species or in the form of complexes. The composition comprises one or more proteins, peptides and variants thereof have at least one amino acid sequence defined by SEQ ID NOS: 1–6 or portions thereof. In one embodiment, the composition comprises one or more proteins, peptides and variants thereof that share amino acid sequence homology with at least one heterogeneous nuclear ribonucleoprotein. In the case of complexes, the complex of protein, peptides and variants thereof may be held together by covalent or noncovalent bands. One or more protein and variants thereof may form the complex. In one embodiment of the complex comprises at least one protein, peptide or variant thereof that shares amino acid sequence homology with hnRNP A2. In another embodiment the complex comprises at least one protein, peptide or variant thereof that shares amino acid sequence homology with hnRNP B1. In yet another embodiment, the complex comprises a protein, peptide or variant thereof that shares amino acid sequence homology with hnRNP A2 and a second protein, peptide or variant thereof that shares amino acid sequence homology with hnRNP B1.

The present invention provides methods of purifying an epithelial cancer protein, peptides and variants thereof, which are early markers for cancer, that achieves high levels of purification. The methods described herein achieve at least 20,000 fold purification, preferably 25,000 fold purification, more preferably greater than 25,000 fold purification compared to the source material.

The method of purification takes steps to prevent or inhibit degradation of the protein, peptide or variant thereof during the purification process. For successful purification of the epithelial protein, peptide or variant a large amount of starting material is preferred. In one embodiment, the purification was made possible by the use of enormous numbers of p31 expressing tumor cells approximately greater than about $2.5 \times 10^{11}$ cells.

The protein, peptides and variants thereof may be used in diagnostic methods and in in vitro assays to detect the presence of a similar protein, peptide and variants thereof present in a biological sample. The assays allow for early detection of pre-neoplastic and neoplastic cells and in defining the process of carcinogenesis.

In one embodiment, the isolated and purified protein, peptide or variant thereof is useful in immunoassays for the detection of the corresponding protein or variant thereof. The immunoassays are qualitative and quantitative. The immunoassays are useful in detection of precancer and cancer cells in which an increase in the quantity of the epithelial protein, peptide or variant thereof is indicative of precancer and cancer. Conversely, the immunoassays are useful in monitoring the efficacy of cancer treatment or intervention in which the absence or decrease in the quantity of the epithelial protein, peptide or variant thereof recovered from a patient undergoing treatment or intervention is an indication of an efficacious treatment.

Immunoassays of the present invention may be a radioimmunoassay, Western blot assay, immunofluorescent assay, enzyme immunoassay, chemiluminescent assay, immunohistochemical assay and the like and may be performed in vitro, in vivo or in situ. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, *J. Clin. Chem. Clin. Biochem.*, 22:895–904. Biological samples appropriate for such detection assays include, but are not limited to, cells, tissue biopsy extracts, whole blood, plasma, serum, sputum, cerebrospinal fluid, pleural fluid, urine and the like.

In one embodiment for detection using a competitive immunoassay, test sample suspected of containing the epithelial protein, peptide or variant thereof is reacted in fluid phase with an antibody known to be reactive with the protein, peptide or variant thereof to form an antigen-antibody complex. This fluid phase is then placed on a solid phase reagent having surface bound protein, peptide or variant of the invention. Any antibody which is not in the form of a complex is free to bind to the surface bound protein, peptide or variant thereof. The amount of antibody bound to the surface is determined by methods known in the art. The solid surface reagent can be prepared by known techniques for attaching protein to solid support material. These attachment methods include but are not limited to non-specific adsorption of the protein or variant to the support or covalent attachment of the protein or variant to the solid support. In one embodiment, the antibody is 703D4 disclosed in U.S. Pat. No. 4,569,788.

The label may be an enzyme which is detected by incubating the solid support in the presence of a suitable fluorimetric or colorimetric reagent. Other detectable labels may be used, such as radiolabels or colloidal gold and the like.

The protein, peptide and variants thereof may be prepared in the form of a kit, alone, or in combination with other reagents such as antibodies, for use in the immunoassay.

The protein, peptide and variants thereof may be used to elicit specific antibodies and antigen binding fragments thereof that are immunoreactive with the epithelial protein, peptide or variant thereof. Of particular importance are antibodies or antigen binding fragment thereof that recognize an epitope which is associated with transformation of a normal cell to a pre-cancer cell. The epitope is not present or is present in low amounts in normal cells and is highly expressed in precancer and cancer cells. In one embodiment the antibody or antigen binding fragment thereof reacts with an epithelial protein, peptide or variant thereof having a post-translational modification, wherein said post-translational modification is indicative of a precancer or cancer cell. The antibodies may be produced by methods disclosed in U.S. Pat. No. 4,569,788 or by other methods known in the art. Such antibodies are useful in immunoassays to detect the epithelial protein and to detect post-translational modifications of the protein. The antibodies or antigen binding fragment thereof are useful as intermediate end-point markers in determining the efficacy of a cancer treatment or intervention.

The invention provides a purified and isolated DNA molecule comprising all or part of the nucleic acid sequence that encodes an epithelial protein, peptide or variant thereof, whose expression or overexpression is indicative of a precancer or cancer cell.

Amplifications were done with gene libraries from 3 sources including two lung cancer cell lines, NCI-H157 and NCI-H720, which were the two cell lines used to purify the antigen, p31. As a control, the gene from a short term culture of normal bronchial epithelial cells was also amplified (Clonetics NHBE 2129 cells, San Diego, Calif.). These genes were then inserted into a pCR II vector and grown up in E. coli using the original TA Cloning® Kit, Cat. No. C2020-3 Lot No. 411208 from Invitrogen Corp., San Diego, Calif. The transformation cultures from the three different sources of hnRNP genes A2/B1 and the three plasmid containing the hnRNP genes were deposited under conditions of the Treaty of Budapest at the American Type Culture Collection, 12301 Parklawn Dr., Rockville, Md. on Oct. 2, 1995. The sequence for the primers used to amplify the entire hnRNP genes was as follows:

CTA CAG CGC CAG GAC GAG T (SENSE)
CCC ATG GCA AAT AGG AAG AA (ANTI SENSE)

These primers allowed for the amplification of the full length of both the A2/B1 genes.

In one embodiment the isolated DNA or portion thereof encoding the epithelial protein is substantially homologous to portions of the sequences disclosed in FIGS. 1–3. It is anticipated that the nucleic acid sequence of the present invention varies to a certain extent from that depicted on FIGS. 1–3. The sequences on FIGS. 1–3 were derived from a cDNA clone from a malignant human osteosarcoma cell line. The present invention encompasses the DNA or portion thereof isolated from normal cells and premalignant cells.

Due to the degeneracy of the genetic code, it is to be understood that numerous choices of nucleotides may be made which will lead to a DNA sequence capable of directing the production of the instant epithelial protein, peptide and variants thereof. As such, DNA sequences which are functionally equivalent to the sequence set forth herein or which are functionally equivalent to sequences which would direct the production of analogs of the epithelial protein are intended to be encompassed within the present invention.

The present invention also provides a recombinant DNA molecule and a vector capable of being propagated and expressed in a prokaryotic or a eukaryotic host cell. Expression vectors suitable for use in the invention comprise at least one expression control element operationally linked to the nucleic acid sequence or part thereof. Expression control elements are inserted in the vector to control and regulate the expression of the nucleic acid sequence. Examples of expression control elements include, but are not limited to, the lac system, operator and promoter regions of phage lambda, yeast promoters, and promoters derived from vaccinia virus, adenovirus, retrovirus, or SV40. Other operational codons, polyadenylation signals, and other sequences required for the appropriate transcription and subsequent translation of the nucleic acid sequence in a given host system are present. In addition, it is understood that the expression vector contains any additional elements necessary for the transfer and subsequent replication of the nucleic acid containing expression vector in the host system. Examples of such elements include, but are not limited to, origins of replication and selectable markers. Such expression vectors are commercially available or are readily constructed using methods known to those in the art (e.g. F. Ausubel et al, 1987 in: "Current Protocols in Molecular Biology", John Wiley & Sons, New York, N.Y.). Examples include, but are not limited to vaccinia virus vectors, adenovirus vectors, herpes virus vectors and baculovirus vectors. The recombinant expression vector containing all or part of the nucleic acid sequence encoding the epithelial protein, peptide or variant thereof is transformed, transfected or otherwise inserted into a host organism or cell. The host cells transformed with the nucleic acid sequence encoding the epithelial protein of the invention include eukaryotic cells such as animal, plant, insect, algae, and yeast cells, and prokaryotic cells such as E. coli, B. subtilus and the like. Preferred eukaryotic host cells include but are not limited to, COS cells, CHO cells, insect cells, bronchial epithelial cells, especially eukaryotic cells that allow for post-translational modifications of the expressed epithelial protein, peptide or variants thereof. The means by which the vector carrying the nucleic acid sequence may be introduced into a cell include, but is not limited to, microinjection, electroporation, transduction or transfection using DEAE-dextran, lipofection, calcium phosphate or other procedures known to the use skilled in the art (Sambrook et al, 1989, in: Molecular Cloning. A Laboratory Manual", Cold Spring Harbor Press, Plainview, N.Y.).

The expressed recombinant epithelial protein, peptides or variants thereof may be detected by methods known in the art, including but not limited to, Coomassie blue staining, silver staining and Western blot analysis using antibodies specific for the epithelial protein, peptides or variants thereof as described herein.

The recombinant epithelial protein, peptides and variants thereof of the present invention may be isolated and purified using the protocol described herein including anion exchange chromatography, preparative isoelectric focusing, polymer-based $C_{18}$ HPLC and analytic $C_4$ HPLC.

The genes or gene products of epithelial protein, peptides or variants thereof can be detected in mammalian biological samples such as blood, serum, stool, urine, amniotic fluid, sputum, bone tissue biopsy specimens and the like. Of particular interest is the detection of an epithelial protein, peptide or variant thereof having sequence homology with at least one hnRNP gene or gene product. By screening body samples, early detection of precancer cells may be achieved and in turn early treatment may be provided to the mammal to inhibit or prevent transformation of the precancer cells to a cancer cells. In addition, the efficacy of chemotherapy and/or radiotherapy can be monitored by testing of body samples for the altered expression or overexpression of the genes or gene products.

A predisposition to cancer may be ascertained by testing mammalian biological samples for altered expression and/or overexpression of a gene encoding the epithelial protein, peptide or variants thereof. This predisposition can be determined by testing DNA or RNA from cells removed from any tissue or fluid from the mammal to detect overexpression and/or variant expression products of the epithelial protein, peptide or variants thereof. The method of diagnosis of the present invention is applicable to any cancer in which the epithelial protein, peptide or variants thereof have a role in tumorigenesis. Of particular interest are lung cancer, bone cancer, renal cancer, breast cancer, uterus, prostate, colon, melanoma, myeloma and the like.

In the method of diagnosing a genomic nucleic acid sequence isolated from a biological sample taken from a mammal is contacted with the nucleic acid sequence or portion thereof encoding an epithelial protein which is an early marker for cancer, under conditions that allow hybridization between the sequences and detecting the hybridized sequences. The presence of a genomic nucleic acid sequence or the presence of an altered genomic nucleic acid sequence as compared to a normal nucleic acid sequence is indicative of precancer or cancer in the mammal. The increased presence of the DNA, mRNA and/or alternate splice forms of the mRNA in the biological sample is indicative of precancer and cancer in the mammal.

The oligonucleotides of the present invention are useful in detection of the gene and detection of alterations or mutations in the gene encoding the epithelial protein. The oligonucleotides may also be used to monitor the response of epithelial cells to cancer treatment and intervention and as such are important intermediate endpoint markers.

In another aspect of the invention, oligonucleotide primers are useful for the synthesis of all or a portion of the gene encoding the epithelial protein, peptide or variants thereof using the polymerase chain reaction. A pair of single stranded DNA primers can be annealed to sequences within or surrounding a gene in order to amplify DNA synthesis of the gene. The polymerase chain reaction is known in the art as described by Saiki et al., 1988 *Science* 239:487491; U.S. Pat. No. 4,683,202 and U.S. Pat. No. 4,683,195 and *Methods in Enzymology*, 155:335–350, 1987. Specific primers which can be used to amplify the gene include but are not limited to:

| | |
|---|---|
| 5'GAGTCCGGTTCGTGTTCGTC3' | (SEQ ID NO.: 11); |
| 5'TGGGCTCTCATCCTCTCCTATTA3' | (SEQ ID NO.: 12); |
| 5'CTACAGCGCCAGGACGAGT3' | (SEQ ID NO.: 13); |
| 5'CCCATGGCAATAGGAACAA3' | (SEQ ID NQ.: 14); |
| TGTTCTGTTACCTCTGGGCTCTCA | (SEQ ID NO.: 15); | and the like.

Specific pairs of primers may be used to clone the cDNA encoding the epithelial protein, peptide and variants of the present invention. Examples of primer pair that may be used to clone the cDNA using PCR include but are not limited to SEQ ID Nos: 11 and 12; SEQ ID Nos: 13 and 14; SEQ ID Nos: 11 and 15; and the like.

The gene for hnRNP A2 as well as for the gene for B1 have been recovered from a PCR reaction with a library of genes created from the cell line NCI-H157, NCI-H720 as well and a short term culture of bronchial epithelial cells. These genes have been inserted into a vector (PCRII) and expressed in *E. coli*. The presence of the appropriate gene product has been confirmed by PCR with a set of conserved hnRNP primers (used a Sense primer 5-3, GCTCGGCT-GCGGGAAATC and anti sense primer, TAAGCTTTC-CCCATTGTTCGTAGT with an expected 146 bp PCR product). The plasmids containing these genes are on deposit at ATCC under the conditions of the Treaty of Budapest. The differences in the gene sequences from the cancer cell lines relative to the gene obtained from normal bronchial cells are to be determined. We will evaluate to exclude the possibility of a contribution from a mutation present only in the malignant cell lines as to the role of hnRNP A2/B1 mutation to the process of carcinogenesis.

In addition, the protein product may be expressed of the hnRNP A2/B1 gene from the cancer cell line NCI-H157 and NCI-H720 in an expression system that has the metabolic machinery to process the post translational changes in the gene product. The final protein is compared with the product of the hnRNP A2/B1 gene product from the normal bronchial cell line. The protein is purified from those different cell sources, cyanogen bromide digestion performed and then the products analyzed using one or two dimensional gel electrophoresis or mass spectrometry. Any difference in the gene product from NCI-H157 or H720 compared to the normal source of the hnRNP could be due to a critical mutation.

Also, combinations of oligonucleotide pairs based on the nucleic acid sequence encoding the epithelial protein or portion thereof may be used as PCR primers to detect mRNA in a biological sample using the reverse transcriptase polymerase chain reaction (RT-PCR) process for amplifying selected RNA nucleic acid sequences as detailed herein as well as in Ausubel et al, 1987 In: "Current Protocols In Molecular Biology" Chapter 15, John Wiley & Sons, New York, N.Y. The oligonucleotides can be synthesized by automated instruments sold by a variety of manufacturers.

The present invention also encompasses in situ PCR and in situ RT-PCR for detection of DNA and RNA encoding the epithelial protein, peptides and variants thereof. The technique is preferred when the copy number of a target nucleic acid is very low, or when different forms of nucleic acids must be distinguished. The method is especially important in detecting and differentiating precancer and cancer cells from normal cells. The method is also useful in detecting subsets of epithelial cells destined to become cancer cells. Confirmation of in situ PCR product identity is accomplished by in situ hybridization with a nested $^{32}$P-labeled probe or by examining the products using Southern blot analysis to corroborate predicted base pair size. Coordinate transcriptional/translational expression is demonstrated by sequential in situ RT-PCR/immunohistochemical analysis on serial tissue sections.

Overexpression of the genes and the resultant overactivity of the gene product may contribute to deregulation of cell growth and neoplasia. Therefore, the present invention also provides antiserse oligonucleotides which may be particularly useful in specifically regulating the expression of the gene encoding the epithelial protein.

As used herein, antisense therapy refers to administration or in situ generation of DNA or RNA oligomers or their derivatives which bind specifically to a target nucleic acid sequence. The binding may be by conventional base pair complementary, or, for example, in the case of binding DNA duplexes, through specific interactions in the major groove of the double helix. By specifically binding to its target DNA or RNA, the function of DNA or RNA is inhibited or suppressed.

The antisense oligonucleotides of the present invention may vary in the number of nucleotide residues and may range from about 3 to about 100 nucleotide residues, preferably ranging from about 3 to about 50 nucleotide residues, more preferably from about 3 to about 25 nucleotide residues. In one embodiment the oligonucleotide has less than about 20 nucleotide residues. In another embodiment, the oligonucleotide has about 15 to about 20 nucleotide residues.

Antisense oligonucleotides of the present invention are constructed to prevent the expression of the epithelial protein, peptide or variant thereof that is a marker for early detection of cancer. Antisense oligonucleotides of the invention are nucleotides that bind and prevent or inhibit the transcription and/or translation of the nucleic acid encoding the epithelial protein. Of particular interest are antisense oligonucleotides that bind and prevent or inhibit the transcription and/or translation of one or more of secondary structures analogous to the structures of hn-RNP as defined by Burd, C. G. et al. *Science*, vol. 265, pp. 615–621, 1994, of arginine-rich motif, RGGbx, α2, TI, and β4 regions of hn-RNP.

hnRNP A2/B1 have been implicated in a variety of cellular functions that could be important in the process of carcinogenesis. These functions include the regulation of alternative splice site switch activity, RNA (DNA)-protein interactions, and RNA (DNA) annealing. In particular, hnRNP A/B proteins are major nuclear proteins binding with high affinity to teleomeric DNA repeats $(TTAGGG)_n$ and to the RNA equivalent $(UUAGG)_n$. AntiSense strategies to modulate the gene coding region for the part of the hnRNP A/B protein involved in splice site regulation or interactions with telomeric binding would be steps to inhibit the role of hnRNP A/B proteins in progressive carcinogenesis. Targets for anti sense strategies include the G domain as this has a major effect on hnRNP function. This region is largely comprised of repetitive, imperfect iterations of the motif $(GN^F_Y GG^S_G RG)$ (n=12). This glycine-rich region of the hnRNP molecule greatly affects protein functions such as nucleotide binding including interaction with the telomeric regions. (Ishikawa, F et al *Mol. Cell. Biol.* Vol. 13, 4301, 4310, 1993; McKay, S. J. et al *Nucleic Acids Res.* Vol. 20:6461–64, 1992). Antisense strategies to inhibit cancer would inhibit the translation of these hnRNP regions.

These same regions that are critical to the role of the hnRNP A2/B1 genes to carcinogenesis would also be rational targets for developing peptide antagonists to block the function of these two gene products. The peptide antagonists would target the comparable regions of hnRNP protein that has just been discussed for the hnRNP gene.

The antisense oligonucleotides comprise a nucleic acid sequence which is anticomplementary to the nucleic acid sequence encoding the amino acid sequences: ATVEEVDAAMNARPHKVDGRVVEPKRAVS (SEQ ID NO.:16) or portions thereof; DDHDSVD-KIVIQKYHTVNGHNCEVRKALS (SEQ ID NO.: 17) or portion thereof, and the like.

Examples of antisense oligonucleotides of the present invention include but are not limited to nucleic acid sequences anti complementary to the sequence or portion thereof of hn-RNPA1, A2, B1 of FIGS. 1–3.

The oligonucleotides of the present invention may contain at least one or more modified linking group, sugar residue and/or base. The modified oligonucleotides of the invention, are resistant to degradation under both physiological and tissue culture conditions, and in particular are resistant to degradation by exonucleases. Such modifications include but are not limited to methyl phosphorothioate internucleotide linkages, phosphorothioate linkages, phosphoramidate internucleotide linkages, a 3' end cap and a 3' hair-pin loop structure. Such modified oligonucleotides and methods for production thereof are described in U.S. Pat. Nos. 5,264, 562, 5,194,599 and 5,256,775, Padmapriya and Agrawal, *Bio Org. & Med. Chem. Lett.*, 3, 761 (1993), Temsamani et al., *Ann. N.Y. Acad. Sci.*, 660, 318 (1992), Tang et al., *Nucleic Acids Res.*, 21, 2729 (1993). Examples of such modified oligonucleotides include but are not limited to oligonucleotide methylphosphorothionates, 3' end-capped oligodeoxy nucleotide phosphorothioates and oligonucleotide phosphorothioates having a hair-pin loop structure at their 3' ends.

The oligonucleotides of the present invention may also be modified by the addition of groups to facilitate their entry into cells. Such groups include but are not limited to, non-polypeptide polymers, polypeptides, lipophilic groups and the like. Lipophilic groups refer to moieties which are chemically compatible with the outer cell surface, i.e., so as to enable the oligonucleotide to attach to, merge with and cross the cell membrane. Examples of such lipophilic groups are fatty acids and fatty alcohols, in addition to long chain hydrocarbyl groups. Such modified oligonucleotides and methods for making are disclosed in U.S. Pat. No. 5,256, 775.

Cancers which may be treated using the oligonucleotides or mixtures thereof include but are not limited to melanoma, metastases, adenocarcinoma, thymoma, lymphoma, lung cancer, liver cancer, colon cancer, kidney cancer, pancreatic cancer, brain cancer and the like. Of particular interest using the oligonucleotides of the invention include cancers that are associated with overexpression of the hnRNP gene product or expression of the altered gene product.

In the method of treatment, the administration of the oligonucleotides of the invention may be provided prophylactically or therapeutically. The oligonucleotide or mixtures thereof may be provided in a unit dose form, each dose containing a predetermined quantity of oligonucleotides calculated to produce the desired effect in association with a pharmaceutically acceptable diluent or carrier such as phosphate-buffered saline to form a pharmaceutically composition. In addition, the oligonucleotide may be formulated in solid form and redissolved or suspended prior to use. The pharmaceutical composition may optionally contain other chemotherapeutic agents, antibodies, antivirals, exogenous immunomodulators or the like.

The route of administration may be intravenous, intramuscular, subcutaneous, intradermal, intraperitoneal, intrathecal, ex vivo, and the like. Administration may also be by transmucosal or transdermal means, or the compound may be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays, for example, or using suppositories. For oral administration, the oligonucleotides are formulated into conventional oral administration forms, such as capsules, tablets and tonics. For topical administration, the oligonucleotides of the invention are formulated into ointments, salves, gels, or creams, as is generally known in the art.

In providing a mammal with the oligonucleotide of the present invention, preferably a human, the dosage of administered oligonucleotide will vary depending upon such factors as the mammal's age, weight, height, sex, general medical condition, previous medical history, disease progression, tumor burden, and the like. The dose is administered as indicated. Other therapeutic drugs may be administered in conjunction with the oligonucleotide.

The efficacy of treatment using the oligonucleotide may be assessed by determination of alterations in the concentration or activity of the DNA, RNA or gene product of epithelial protein, peptide or variant thereof, tumor regression, or a reduction of the pathology or symptoms associated with the cancer.

In addition, to use as a therapeutic, the oligonucleotides of the invention may be used as diagnostic reagents to detect the presence or absence of the DNA, RNA or portion thereof of the epithelial protein, peptide or variant thereof to which the oligonucleotide is complementary. Of particular interest is the detection of at least one hnRNP or portion thereof. Such diagnostic tests are conducted by binding of the oligonucleotide to its specific target molecule which is then detected by conventional means. For example, the oligonucleotide may be labeled using radioactive, fluorescent, chemiluminescent, or chromogenic labels and the like and the presence of the label detected. The presence of the target molecule may be detected in vitro or in vivo.

Another aspect of the invention is a method of overexpressing the gene encoding the epithelial protein, peptide or variant thereof by the introduction of the gene or multiple copies of the gene into a low expressing cell line such as short term culture of normal bronchial, mammary, colon cells, NIH 3T3 cells, and the like. Of particular interest are normal low expressing cell lines obtained from lung, breast, kidney, skin, bone, prostate, ovary and the like for incorporation of the gene. The introduction of the gene is accomplished by placing the gene in an expression vector such as PCRII and transfecting the vector into the low expressing cell line. Features associated with a transformed phenotype such as clonogenially, loss of contact inhibition and tumorigenicity in nude mice is evaluated. Overexpressor cell lines showing a precancer or cancer phenotype are useful in screening for therapeutic agents that down regulate expression of the epithelial protein.

The invention also provides a transgenic animal which has incorporated into its genome one or more copies of the gene encoding an epithelial protein, peptide or variant thereof which is an early marker for cancer. The general method of producing transgenic animal is described in Krimpenfort et al U.S. Pat. No. 5,175,384, Leder et al. U.S. Pat. No. 5,175,383, Wagner et al. U.S. Pat. No. 5,175,385, Evans et al. U.S. Pat. No. 4,870,009 and Berns U.S. Pat. No. 5,174,986. The incorporation of the gene results in overexpression, altered expression or expression of multiple forms or variants of the epithelial protein. The resulting transgenic animal is prone to develop cancer and may develop cancer at an accelerated rate at one or more locations of the body. This model will allow elucidation of up and downstream biology of hnRNP and epithelial proteins sharing sequence homology with at least one or more hnRNP. These experiments could provide additional confirmatory biomarkers for early detection as well as additional targets for re-regulating the transformed cells. The animal model is also useful in screening chemotherapeutic drugs for cancer treatment.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of the equivalents of the disclosed embodiments.

All references and patents referred to are incorporated herein by reference.

EXAMPLE 1

Materials and Methods

Electrophoresis and Western Blotting:

703D4 is an IgG2b$_k$ monoclonal antibody[6]. The antibody was affinity purified from mouse ascites using a Protein A sepharose column and a discontinuous glycine NaCl/citrate gradient. To analyze the antigen purification, an aliquot of the starting material and of each of the purification steps described below (ion exchange, IEF, and HPLC) were assayed by either Tris-Tricine or Tris-Glycine-SDS polyacrylamide gel electrophoresis (SDS-PAGE). Aliquots were freeze-dried and reconstituted or diluted directly in either tris-glycine sample buffer containing 5% mercaptoethanol or tricine sample buffer and electrophoresed on a 10–20% Tricine or 4–20% Tris-glycine gel (NOVEX). Proteins on duplicate gels were electrophoretically transferred to PVDF membrane at 30V for 1.5–2.0 hours, stained with Coomassie brilliant blue or blocked overnight at 4° C. with 1% bovine serum albumin in phosphate buffered saline and immunoblotted using the mouse monoclonal antibody 703D4(6). The bound antibody on the western transfer PVDF membranes was detected using direct binding of radioiodinated staphylococcal Protein A. Blots were imaged on a Phosphorimager (Molecular Dynamics, Calif.) and on Kodak XAR and XRP film.

Preparation of Cellular Subfractions:

Human tumor cell lines, including the NSCLC cell lines NCI-H720 (carcinoid) and NCI-H157 (squamous ATCC CRL-5802) used for antigen purification, were grown in RPMI-1640 medium (Gibco) supplemented with 5% fetal calf serum at 37° C. and 5% $CO_2$. The cells were harvested and washed twice with iced Dulbecco's Phosphate-buffer solution (pH7.4) and resuspended in MES buffer (17 mM morpholinoethanesulfonic acid), 20 mM EDTA, 250 mM sucrose] and homogenized in a hand-held homogenizer. Trypan blue exclusion was employed to ensure greater than 90% cell lysis following homogenization. The lysates were transferred to Beckman polyallomer centrifuge tubes, and centrifuged at 150,000×g for 60 min using a Beckman XL90 ultracentrifuge and SW41 rotor. The pellet containing the membrane and nuclear fractions were retained, and the cytosolic supernatant was discarded [Krajewski, 1993, Cancer Res. 53:4701–4714].

The pellet fractions were resuspended in extraction buffer (0.015 M NaCl, 10 mM Tris pH7.4, 5 mM EDTA) containing 1% Tween-20. The samples were incubated on ice for one hour with frequent vortexing, and centrifuged at 16,000×g for 20 minutes. The supernatants were then diluted 3 times with DI water and adjusted to pH 6.5.

Ion-exchange Chromatography and Liquid Phase Isoelectric Focussing:

A Dupont Bio Series WAX (weak anion exchange) column (MacMod, Chads Ford, Pa.), equilibrated with Tris-HCl pH 6.5, was used. Detergent-solubilized proteins were pumped through the column at 2.0 mL/min, and fractions were pooled and freeze dried. 703D4 immunoreactive material bound weakly to the resin in the presence of 50 mM NaCl, and was eluted in the unbound material from this column.

Fractions positive antigen were resuspended to a final volume of 45 ml with 4 M urea containing 3% CHAPS, 10% Glycerol, and 0.8% ampholines pH range 3–10 (Bio Rad, Richmond, Calif.). This protein-ampholyte cocktail was loaded to a chilled Rotofor preparative isoelectric focusing (IEF) apparatus (Bio-DAD, Richmond, Calif.) which was operated at a constant twelve watts. One hour after the maximum voltage was reached, usually 1200V, fractions were harvested by vacuum collection. Run time was approximately four hours. pH values were determined for the twenty fractions which were harvested. 703D4 antigen was concentrated in fractions with pH 8–9. The two most positive fractions from each of three IEF runs (three batches of cells) were pooled for HPLC purification.

HPLC:

All organic solvents used were HPLC grade (Burdick & Jackson, Muskegon, Wis.). The isoelectric focussing fractions positive for antigen were diluted two-fold with 18 Mohm water, acidified with 1% trifluoroacetic acid (TFA) (Pierce Chemical Co., Rockford, Ill.), and applied to a 10 mm×10 cm Poros perfusion polymeric $C_{18}$ column (PerSeptive Biosystems, Framingham, Mass.) which was equilibrated with 5% acetonitrile/0.1% TFA. The protein was eluted using a twenty minute linear gradient proceeding from 5% acetonitrile/0.1% TFA to 100% acetonitrile/0.1% TFA at a flow rate of 15 ml/minute (the limit of the pumping system). Fractions of 2.5 mLs (15 secs) were collected after a 2.0 min wash. Next, the positive fractions (2.5–5.0 mLs, ca. 40% acetonitrile) were diluted five fold with water/0.1% heptafluorobutyric acid (HFBA) (Pierce Chemical Co., Rockford, Ill.) and applied to the another Poros polymeric $C_{18}$ column equilibrated with 5% methanol/0.1% heptafluorobutyric acid (HFBA) (Pierce Chemical Co., Rockford, Ill.). The protein was eluted with a twenty minute linear gradient from 5% methanol/0.1% HFBA to 100% methanol/0.1% HFBA at a flow rate of 15 ml/minute. The 703D4 antigen eluted at approximately 80% methanol.

As the last stage in the purification, the positive fractions were applied to a 2.1 mm×25 cm Vydac analytical $C_4$ column (Vydac, Hesperia, Calif.) which was equilibrated with 20% acetonitrile/0.1% TFA, and the protein eluted with a linear gradient from 20% acetonitrile to 70% acetonitrile over 150 minutes (0.3%/min), at a flow rate of 0.2 ml/minute.

Digestion and Protein Sequencing:

Several failed attempts at obtaining N-terminal amino acid sequence information, both on SDS-PAGE blotted material and directly from the fractions at the last $C_4$ HPLC step, indicated that the N-terminus of the purified protein was blocked. Therefore a cyanogen bromide (CNBr) digestion was employed to obtain internal sequence. The purified protein, freeze-dried after the $C_4$ HPLC fractionation, was cleaved under nitrogen with 0.15 M CNBr (Fluka) in 70% formic acid at room temperature for twenty-four hours [Gross, 1974, Biochem. Biophys. Res. Commun. 59, 1145–50]. The resulting peptides were separated by 16% Tricine SDS-PAGE and electroblotting onto PVDF membrane. The peptides were visualized using Ponceau S and representative bands excised for Edman degradation sequence analysis on an Applied Biosystem model 477A. Amino acid sequence obtained was compared to known sequences in the SwissProt data base using PepScan (PE/SCIEX, Thornhill, Ont., Canada).

Isolation of Total Cellular RNA and Northern Analysis:

RNA was extracted by guanidium isothiocyanate/2-mercaptoethanol and purified by ultracentrifugation as previously described [Davis et al, 1986, Preparation and analysis of RNA from eukaryotic cells. Basic methods in molecular biology, New York, Elsevier, Science Publishing Co., Inc. 129–156]. After ultracentrifugation the RNA pellet was resuspended in water, ethanol precipitated in the presence 0.3 M sodium acetate and pelleted by centrifugation. The dried pellets were redissolved in water, and 10 µg of total cellular RNA from each of tumor cell lines, normal lung and normal bronchial epithelium primary cultures were used for northern blot analysis. The RNA was resolved using a 1% agarose-formaldehyde gel with 0.2 M 3-N-morpholino-propane sulfuric acid/0.05 M sodium acetate/0.01 M EDTA as the running buffer. The RNA was then transferred to a nitrocellulose membrane, hybridized, washed and autoradiography was performed according to standard techniques.

Northern analysis was carried out using probes prepared by random priming of inserts gel-purified from restriction endonuclease digests of plasmids containing full-length cDNAs for hnRNP-A2 and -A1. Approximately $1 \times 10^6$ cpm/mL of probe was used for each Northern analysis.

RT-PCR and a Southern Blot Analysis:

Reverse transcription was performed with 0.2 µg of DNase-treated total RNA using Superscript according to the manufacturer's protocol (Gibco). The resulting cDNA was subjected to 35 cycles of polymerase chain reaction (PCR) on a Perkin Elmer GeneAmp PCR System 9600. The primers designed for the amplification were: 5'-GAGTCCGGTTCGTGTTCGTC-3' (SEQ ID NO. :11) and 5'-TGGCAGCATCAACCTCAGC-3' (SEQ ID NO.: 18). These primers were selected using DNA-Star, and were chosen to span a site of alternate exon utilization (36 nt) which generates the hnRNP splice forms -A2 and -B1. (See FIG. 7a) The resulting amplified DNA was analyzed by electrophoresis on a 2.0% NuSieve agarose gel. Transfer to nitrocellulose filter and hybridization, wash and autoradiography were performed as previously described [Davis et al, 1986 ibid]. Southern blot analysis was carried out with a $^{32}$P-end-labelled 20 nt antisense oligonucleotide present in both hnRNP-A2 and -B1. This 22 nt antisense oligonucleotide has the following sequence: GAGAGAGAAAAG-GAACAGTTCC (SEQ. ID NO. 19). Tables 1–3 provide the characteristics a 1164 bp, a 1145 bp and a 1178 bp cDNA product of the present invention and the primers used to produce the cDNA products.

TABLE 1

| 1164 bp cDNA Product | |
|---|---|
| Upper Primer: 20-mer 5'GAGTCCGGTTCGTGTTCGTC3' | (SEQ. ID NO. 11) |
| Lower Primer: 24-mer 5'TGGGCTCTCATCCTCTCCTATTTA3' | (SEQ.ID NO. 12) |

| DNA 250 pM, Salt 50 mM | Upper Primer | Lower Primer |
|---|---|---|
| Primer TM | 54.3° C. | 55.2° C. |
| Primer Overall Stability | −38.7 kc/m | −43.7 kc/m |
| Primer Location | 74 . . . 93 | 1237 . . . 1214 |
| Product Tm - Primer Tm | 24.2° C. | |
| Primers Tm Difference | 1.0° C. | |
| Optimal Annealing Temperature | 56.3° C. | |
| Product Length | 1164 bp | |
| Product Tm (% GC Method) | 78.4° C. | |
| Product GC Content | 46.6% | |
| Product Tm at 6xSSc | 100.0° C. | |

| Product Melting Temperature (% GC Method) | | | | | | |
|---|---|---|---|---|---|---|
| Salt | | | Formamide | | | |
| mM | xSSC | xSSPE | 0% | 10% | 20% | 50% |
| 1 | 0.005 | 0.006 | 50.2 | 43.7 | 37.2 | 17.7 |
| 10 | 0.051 | 0.062 | 66.8 | 60.3 | 53.8 | 34.3 |
| 50 | 0.256 | 0.312 | 78.4 | 71.9 | 65.4 | 45.9 |
| 165 | 0.846 | 1.031 | 87.1 | 80.6 | 74.1 | 54.6 |
| 330 | 1.692 | 2.062 | 92.1 | 85.6 | 79.1 | 59.6 |
| 500 | 2.564 | 3.125 | 95.0 | 88.5 | 82.0 | 62.5 |
| 1000 | 5.128 | 6.250 | 100.0 | 93.5 | 87.0 | 67.5 |
| 195 | 1.000 | 1.219 | 0.0 | % formamide = Tm 88.3° C. | | |

TABLE 2

| Uppper Primer: 19-mer | (SEQ. ID NO. 13) |
| --- | --- |
| 5'CTACAGCGCCAGGACGAGT3' | |
| Lower Primer: 20-mer | (SEQ. ID NO. 14) |
| 5'CCCATGGCAAATAGGAAGAA3' | |

| DNA 250 pM, Salt 50 mM | Upper Primer | Lower Primer |
| --- | --- | --- |
| Primer TM | 52.7° C. | 51.8° C. |
| Primer Overall Stability | −37.8 kc/m | −39.0 kc/m |
| Primer Location | 59 . . . 77 | 1203 . . . 1184 |
| Product Tm - Primer Tm | | 26.8° C. |
| Primers Tm Difference | | 1.0° C. |
| Optimal Annealing Temperature | | 55.6° C. |
| Product Length | | 1145 bp |
| Product Tm (% GC Method) | | 78.6° C. |
| Product GC Content | | 47.0% |
| Product Tm at 6xSSc | | 100.2° C. |

| Product Melting Temperature (% GC Method) | | | | | | |
| --- | --- | --- | --- | --- | --- | --- |
| Salt | | | Formamide | | | |
| mM | xSSC | xSSPE | 0% | 10% | 20% | 50% |
| 1 | 0.005 | 0.006 | 50.4 | 43.9 | 37.4 | 17.9 |
| 10 | 0.051 | 0.062 | 67.0 | 60.5 | 54.0 | 34.5 |
| 50 | 0.256 | 0.312 | 78.6 | 72.1 | 65.6 | 46.1 |
| 165 | 0.846 | 1.031 | 87.2 | 80.7 | 74.2 | 54.7 |
| 330 | 1.692 | 2.062 | 92.2 | 85.7 | 79.2 | 59.7 |
| 500 | 2.564 | 3.125 | 95.2 | 88.7 | 82.2 | 62.7 |
| 1000 | 5.128 | 6.250 | 100.2 | 93.7 | 87.2 | 67.7 |
| 195 | 1.000 | 1.219 | 0.0 | % formamide = Tm 88.4° C. | | |

TABLE 3

| Upper Primer: 20-mer | (SEQ. ID NO. 11) |
| --- | --- |
| 5'GAGTCCGGTTCGTGTTCGTC3' | |
| Lower Primer: 24-mer | (SEQ. ID NO. 15) |
| 5'TGTTCTGTTACCTCTGGCCTCTCA3' | |

| DNA 250 pM, Salt 50 mM | Upper Primer | Lower Primer |
| --- | --- | --- |
| Primer TM | 54.3° C. | 56.8° C. |
| Primer Overall Stability | −38.7 kc/m | −43.1 kc/m |
| Primer Location | 74 . . . 93 | 1251 . . . 1228 |
| Product Tm - Primer Tm | | 24.2° C. |
| Primers Tm Difference | | 2.5° C. |
| Optimal Annealing Temperature | | 56.3° C. |
| Product Length | | 1178 bp |
| Product Tm (% GC Method) | | 78.4° C. |
| Product GC Content | | 46.6% |
| Product Tm at 6xSSc | | 100.0° C. |

| Product Melting Temperature (% GC Method) | | | | | | |
| --- | --- | --- | --- | --- | --- | --- |
| Salt | | | Formamide | | | |
| mM | xSSC | xSSPE | 0% | 10% | 20% | 50% |
| 1 | 0.005 | 0.006 | 50.2 | 43.7 | 37.2 | 17.7 |
| 10 | 0.051 | 0.062 | 66.8 | 60.3 | 53.8 | 34.3 |
| 50 | 0.256 | 0.312 | 78.4 | 71.9 | 65.4 | 45.9 |
| 165 | 0.846 | 1.031 | 87.0 | 80.5 | 74.0 | 54.5 |
| 330 | 1.692 | 2.062 | 92.0 | 85.5 | 79.0 | 59.5 |
| 500 | 2.564 | 3.125 | 95.0 | 88.5 | 82.0 | 62.5 |
| 1000 | 5.128 | 6.250 | 100.0 | 93.5 | 87.0 | 67.5 |
| 195 | 1.000 | 1.219 | 0.0 | % formamide = Tm 88.2° C. | | |

EXAMPLE 2

Biochemical Chracterization of 703D4 Antigen

Preliminary data showed a wide range of expression of the 703D4 antigen in non-small cell lung cancer cell lines, as judged by a solid phase radiobinding assay. All results shown are for purification steps using NCI-H720 cells which grows rapidly as floating clumps of cells in culture medium containing 5% fetal bovine serum, allowing high cell density. After the methods were developed, an identical protocol was followed to purify the antigen from the original immunogen cell line, NCI-H157. 703D4 immunoreactivity at all stages of the purification was detected by SDS-PAGE followed by immunoblot analysis as preliminary attempts to scale up our previously reported immunoprecipitation technique were not successful.

Western blot analysis of crude extract under both reducing and non-reducing conditions revealed a major specific band with mobility of approximately 31 kDa (Bio-RAD) on both reduced tris-glycine and tricine gels (FIGS. 5b and 5e). Our original analysis had suggested a slightly smaller molecule (Mr approximately 31 kDa) on Novex 10.20% tricine gel under different PAGE conditions and 35 kDa on Novex 8–16% tris-glycine gels. Under all conditions only a single major immunoreactive protein was identified, although in the later stages of purification an apparent disulfide-linked homodimer appeared which could be removed by increased reduction, and at the final HPLC steps a minor band of slightly higher Mr was also seen (FIGS. 6b–6c).

Simple subcellular fractionation analysis of 703D4 antigen distribution, according to the method of Krejewski et al., [Krejewski, 1993, Cancer Res. 53, 4701, 4714], showed that except for a cytosolic supernatant all membrane-bound fractions including the nuclear pellet had immunoreactive protein (data not shown). These data parallel immunohistochemical characterization of 703D4 antigen expression in fixed cells, which showed binding to perinuclear and cytosolic sites. The antigen in a NCI-H720 subcellular fraction containing nuclei and membrane-bound proteins could be solubilized by gentle extraction with either non-ionic detergents such as Tween-20, NP-40 and Triton X-100 or ionic detergent such as 1% SDS.

Weak anion exchange chromatography of crude detergent-solubilized proteins at pH6.5, 7.5 and 8.5 indicated all the immunoreactivity of the crude tumor cell extract was eluted in the unbound fraction in the presence of low (50 mM) salt. When the crude antigen was subjected to preparative IEF under denaturing conditions (4.0 M urea) the immunoreactivity appeared in fractions with pH 8–9.

EXAMPLE 3

Punfication of 703D4 Antigen

The protein identified by 703D4 was isolated from NCI-H720 and -H157 cells by a six-step procedure. The first steps were carried out rapidly to prevent degradation of the target molecule by a variety of protease inhibitors or reducing agents. We were not able to completely prevent loss of the molecule. To prevent degradation during the SDS-PAGE and western blot analysis of each fractionation step, the bulk of the material was stored frozen at −30° C. during the analysis. Determination of exact recoveries at each step could not be made using a western-blot analysis method, therefore the overall yield was estimated from the total protein used for purification and the final yield of purified antigen.

A typical purification commenced with 7–10 mLs packed cells, washed with phosphate buffered saline to remove serum proteins present in the cell culture medium. The initial step was subcellular fractionation to remove cytosolic proteins, and gentle detergent solubilization of the membrane-bound fraction. The detergent-solubilized fraction was then diluted to lower the salt concentration and injected onto the weak anion-exchange column. Studies with weak and strong anion and cation exchange resins demonstrated tight binding to cation and strong anion exchange matrices at acidic to neutral pH, but poor recovery of immunoreactive material. Therefore a weak anion exchange resin was used to remove a significant portion (approximately 75%) of irrelevant protein. This prevented loss of immunoreactive protein through co-precipitation at the IEF step. The unbound material was collected, freeze-dried, and redissolved in a denaturing buffer for preparative IEF. IEF concentrated the immunoreactive protein into a basic region of the pH gradient. Several batches of cells were pooled at this point for HPLC purification.

The HPLC chromatograms from the next stages of this procedure are shown in FIG. 5a. Attempts to remove the ampolytes and urea after the preparative IEF by molecular sieve chromatography or direct injection onto silica-based reversed phase HPLC matrices resulted in precipitation of the target protein and loss within the column matrix. The Poros macro-porous polymeric $C_{18}$ column rapidly and efficiently desalted the antigen from the urea/ampholyte cocktail and simultaneously separated 703D4 immunoreactivity from the bulk of the other proteins in the mixture (FIGS. 5a, 5b). Our HPLC procedures utilize mobile phases usually applied to peptide analysis and/or purification, but proved very effective for purification of this protein. The use of the chromatographically "weaker" organic modifier (methanol) with the more lipophilic ion-pairing agent (HFBA) resulted in a distinctly different mobility of the 703D4 antigen to that in the acetonitrile/TFA mobile phase, and also provided selectivity for removal of other proteins present in the sample. The use of these two solvent systems resulted in significantly greater purification of target molecule than either solvent system alone.

Analytical $C_4$ HPLC with an acetonitrile gradient containing 0.1% trifluoroacetic acid was used as the final purification step. 2.5 mL of positive fractions from the methanol/heptafluorobutyric acid polymeric $C_{18}$ column was diluted five fold with water/0/1% TFA, injected onto a Vydac $C_4$ column and eluted with a slow gradient (0.3%/min) acetonitrile in 0.1% trifluoroacetic acid. Immunoblotting analysis of $C_4$ fractions revealed two immunoreactive proteins with distinct sizes as determined by SDS-PAGE (FIGS. 6b and 6c). The lower and later eluting one is the principal immunoreactive protein, and was greater than 95% pure as determined by coomassie staining of the SDS-PAGE gel.

Overall yield of the principal immunoreactive protein from a typical purification, determined by amino acid analysis and N-terminal Edman sequence yield, was 200 pmol. This yield implies an approximately 25,000 fold purification, although as pointed out above this detection system did not allow for an accurate estimate of loss at several of the steps in the procedure.

EXAMPLE 4

Amino-terminal Sequencing of 703D4 Antigen

Figure 8:
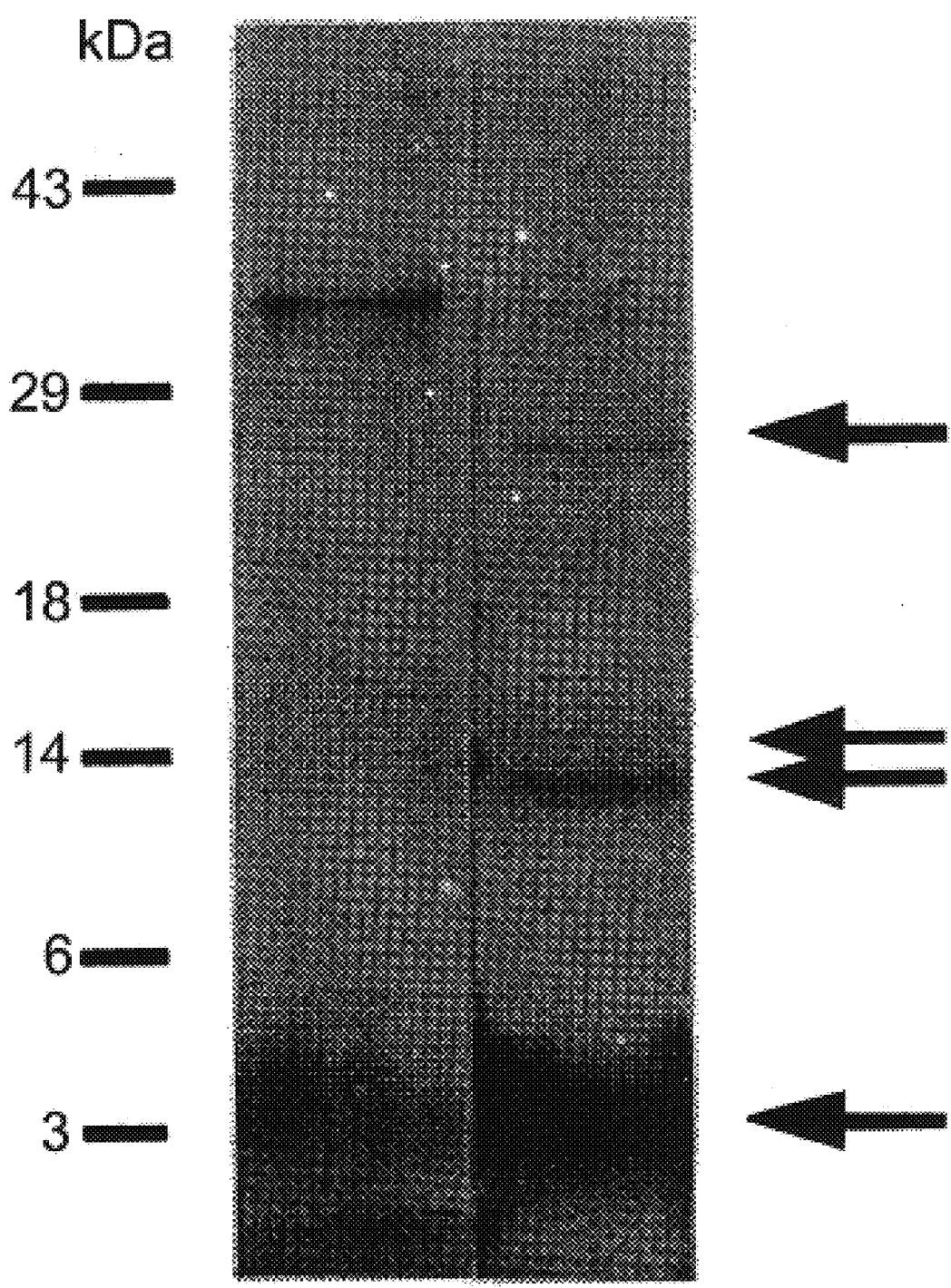
FIG. 8 shows 16% tricine SDS-PAGE analysis of products of CNBr digestion of purified 703D4 principal antigen. Note the left lane is the antigen before digestion, the arrows indicated the four visible bands which subjected to amino-terminal sequencing.

Several attempts to obtain amino-terminal sequence of purified 703D4 antigen were not successful, including direct sequencing from the C4 HPLC fractions. The major immunoreactive protein, that is, the later eluting, lower Mr band on SDS-PAGE of the analytical $C_4$ purification step, was therefore concentrated by freeze-drying the peak fractions and cleaved by CNBr/formic acid. Four bands were separated and visible after Tricine SDS-PAGE on a linear 16% gel, electroblotting onto PVDF membrane, and staining with Ponceau S or Coomassie blue (FIG. 8). All four bands were subject to 12 cycles of Edman degradation on an ABI 477A using the standard ABI protocol for blotted proteins. The sequences revealed were: AARPHSIDGRVV (27 kDa and 13 kDa bands), QEVQSSRSGRGG (15 kDa band) and EREKEQFRKLFI (4 kDa band). The search in SwissProt protein sequence database of each of these sequences identified a single gene product. The sequences, and the size of the cyanogen bromide digestion products, are consistent with the major 703D4 antigen being substantially homologous to the heterogeneous nuclear ribonucleoprotein (hnRNP) A2. FIG. 7a shows these sequences aligned with the translated cDNA sequence of hnRNP B1, which is identical to hnRNP A2 but includes a previously reported 36 nucleotide (12 amino acid) exon close to the protein amino terminus. The 4 kDa CNBr fragment sequence crossed this site of alternate exon splicing, demonstrating the major antigen is substantially homologous to hnRNP A2. As expected for CNBr-generated fragments, each sequence is immediately C-terminal to a methionine residue in the predicted sequence.

The last step in the purification of the 703D4 antigen resolved a second immunoreactive band of slightly higher molecular size, and parallel immunoreactivity (judged by a comparison of Coomasie and immunostaining intensities). A CNBr digestion was carried out on pooled $C_4$ HPLC fractions containing the minor immunoreactive band which eluted slightly before the hn RNP-A2 (pooled from three separate purifications). The CNBr digest yielded two principal Coomasie-stained bands after Tricine SDS-PAGE. The approximate 5 kDa band was Edman sequenced on an Applied Biosystems 494A and yielded a sequence EKT-KEtVPlerKkrE (SEQ ID NO.: 4) (amino acids in upper case represent the primary amino acid in each cycle, and lower case letters denote amino acids identified as the secondary amino acid). This sequence is identical to that of the hnRNP-B1 CNBr fragment which includes the 12 amino acid insertion not present in the hnRNP-A2. A lower level sequence present in the same sample was consistent with hn RNP-A2, which had not been completely resolved from hnRNP-B1 by the $C_4$HPLC (FIG. 6a). The 13 kDa band from the same digest yielded sequences AaRp-s-DGRVr consistent with that expected for the 13 kDa CNBr fragment of hn RNP-A2/B1.

EXAMPLE 5

Analysis of hnRNP A2/B1 Expression

Figure 9A:
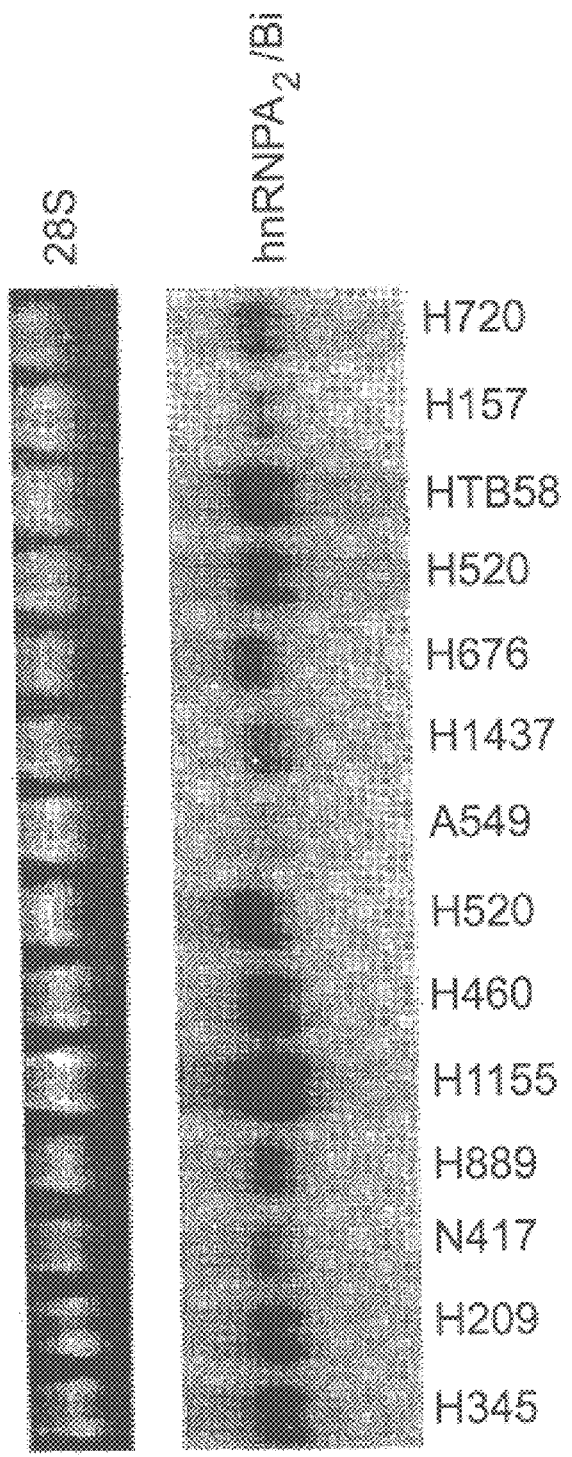
FIG. 9a shows expression of hnRNP-A2/B1 mRNA in lung derived cell cultures. 9a: Northern analysis of NSCLC cell lines (NCI-H720, H157, HTB58, H520, H676, H1437, H549, H820, H4670, HI 155) and SCLC cell lines (NCI-H889, H417, H209, H345). All cells were harvested in station phase and analyzed as described in Materials and Methods. 28S rRNA band visualized under UV illumination used for quantification.

FIG. 9a demonstrates a wide range of expression of hnRNP A2/B1 in both normal and tumor cell lines, and is generally consistent with our radiobinding assays (results not shown).

hnRNP-A2/B1 mRNA is also expressed in the single transformed normal bronchial epithelial cell line tested, and in several normal bronchial epithelial cell primary cultures. Digitized signal intensity of the Northern blot was adjusted for loading differences by quantitation of the 28S rRNA band photographed under UV light and scanned by laser densitometry (Molecular Dynamics Personal Densitometer). Expression of hnRNP-A2/B1 in most tumor cell lines is higher than in the normal lung cell primary cultures analyzed. Both NSCLC and SCLC cell lines express hnRNP-A2/B1 mRNA. Northern analysis using a full-length cDNA probe cannot distinguish hnRNP-A2 from -B1, therefore Rt-PCR was used to confirm that both forms of the gene product are expressed. Results show that all tested cell lines and the normal lung expressed both splice forms, and that hnRNP-A2 appears to be the major form in all cases (FIG. 9b).

Biamonti et al have reported that expression of hnRNP-A1 mRNA, the product of a closely related but distinct gene is subject to proliferation-dependent regulation in normal fibroblasts and lymphocytes but is proliferation-independent in transformed cell lines. Expression of hnRNP-A2/B1 mRNA was analyzed at different stages of cell growth. Cells were harvested in either log phase, or stationary phase one to four days after reaching confluence. The data demonstrate that the levels of the mRNA are proliferation-dependent in all of the lung-derived cells tested (FIG. 10). In 6/6 normal bronchial epithelial cell primary cultures, 1/1 transformed bronchial epithelial cell line, and 3/3 lung tumor cell lines the levels of hnRNP-A2/B1 mRNA fall after the cells leave log-phase growth (FIG. 10).

Figure 9B:
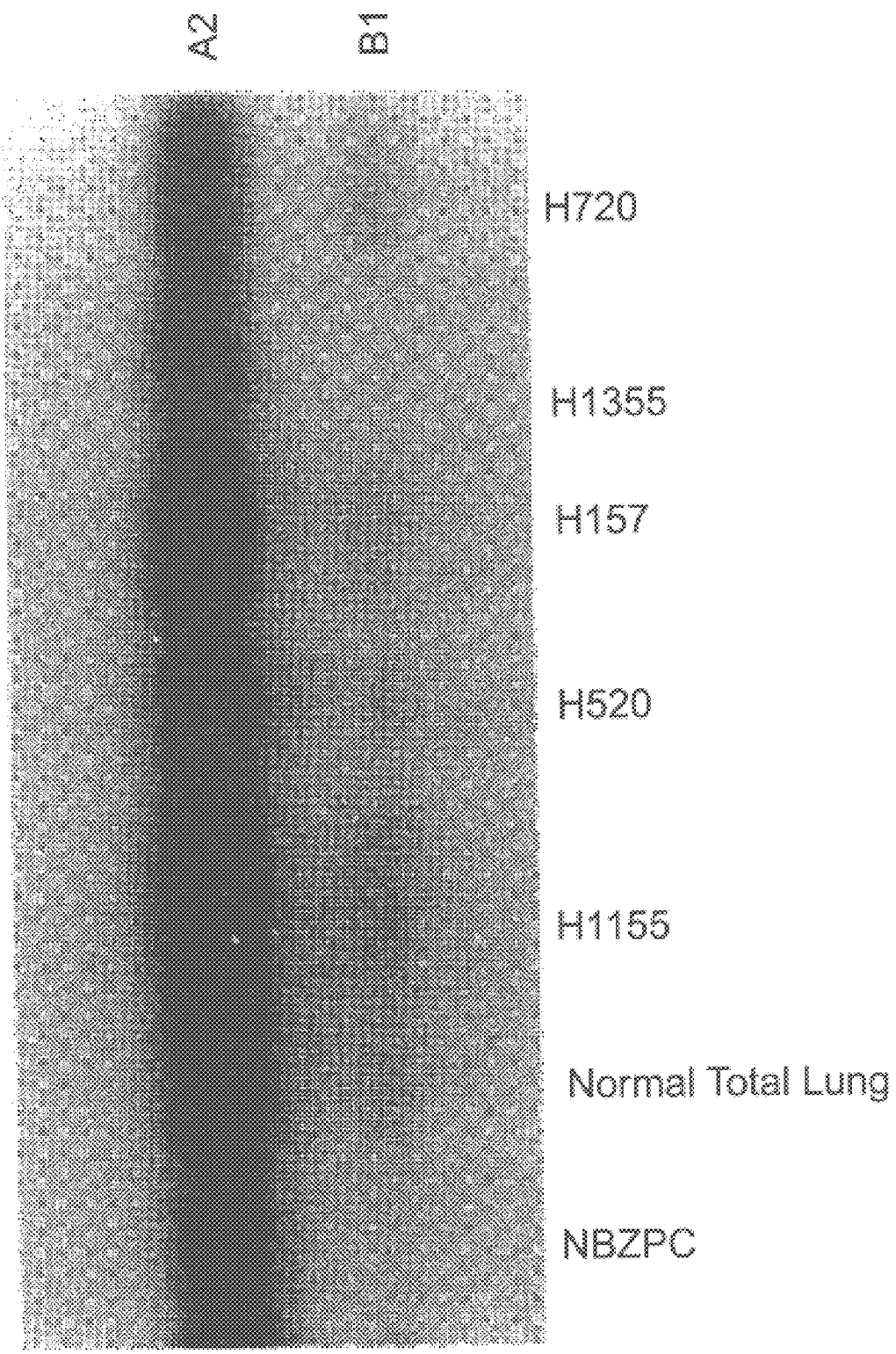
FIG. 9b shows RT-PCR of mRNA from cell lines NCI-H720, H1355, H157, H1155, normal lung and normal bronchial epithelium primary culture. Expected size of the products is 280 bp (hnRNP-A2) and 316 bp (hnRNP-B1). RT-PCR was carried out as described in Materials and Methods. Products were analyzed on 2% agarose TBE-gels, transferred to nitrocellulose, and probed with an end-labelled 20 nt primer common to both hn.RN-A2 and -B1.

The data demonstrate overexpression of hnRNP-A2/B1 in cancer cell lines and in transformed bronchial epithelial cells compared to short term, normal primary bronchial epithelial cell cultures (FIGS. 9a, 9b and 10). Preliminary evidence for hnRNP-A2/B1 showed overexpression in breast tumor cells and transformed breast epithelial cells compared to normal breast epithelial cell primary cultures (data not shown). These findings showed overexpression in several immortalized or transformed cell lines such as epidermal carcinoma cells, promyelocytic cells, SV40 transformed human fibroblasts and teratocarcinoma cell. Rat neuronal cells also expess a high level of hnRNP-A1 mRNA both shortly before and after birth, whereas normal primary fibroblast cultures overexpress hnRNP-A1 only during the logarithmic phase of cell growth (Biamonti, G. et al, *J. Mol. Biol.*, 230, 77–89, 1993). The data demonstrate that although hnRNP-A2/B1 is overexpressed in lung epithelial tumor cells, it is still apparently subject to proliferation-dependent control. Studies on the effect of hnRNP overexpression or knockout on transformation and tumorigenicity are in progress.

Our identification of the 703D4 early lung cancer detection antigen as hnRNP-A2/B1 is provacative in light of the emerging knowledge about the hnRNP group of proteins (Burd, C. G. et al, *Science*, 29, 615–621, 1994). The family of hnRNPs has roles in RNA processing, including pre-mRNA exon splicing and splice site choice, and also in transcription, DNA replication, and recombination (Dreyfuss, et al, *Annu. Res. Biochem.*, 62, 289–321, 1993) (Spector, D. L. *Curr. Opin. Cell. Biol.*, 5, 442–447, 1993). hnRNPs are involved in shuttling mRNA from the nucleus to the cytosol, which is consistent with the subcellular fractionation described here and our previously reported immunohistochemical localization (Katz, D. et al *Nucleic Acid Res.* 22, 238–246, 1994; Pinol-Roma et al *Nature* 355, 730–732, 1992). These roles for the hnRNPs indicate these proteins are integral to cellular proliferation, although the exact mechanism by which hnRNP-A2/B1 is involved in carcinogenesis is not yet clear. Proliferation markers increase in cells responding normally to injury or during fetal growth, and so are not selective for pre-neoplastic carcinogenized cells (Risio, M. J. *J. Cell. Biochem. Suppl.* 166, 79–87, 1992; Ganju, R. K. *J. Clin. Invest.* 94, 1784–1791, 1994). However, our clinical findings of increased levels of hnRNP-A2/B1 in exfoliated bronchial cells from patients whose lungs are in the pre-malignant phases of carcinogenesis indicates a causal role for hnRNP-A2/B1 in the process of carcinogenesis. These data, from several different systems, support a role for hnRNP-A2/B1 and A1/B2 or molecule closely related to these proteins in the expression of the transformation phenotype, and thereby provide a rationale for identification of 703D4 as an early lung tumor detection antibody.

EXAMPLE 6

In Vivo Inhibition of Epithelial Protein Expression and Tumor Growth Rate in Murine Systems In one embodiment, epithelial protein expression and tumor growth rate inhibition may be demonstrated in the following manner. H-157 or H720 tumor cell line known to express high levels of the epithelial protein is injected subcutaneously into the flanks of Balb/C (strain) mice. The antisense oligonucleotide (SEQ ID NO.: 5'TAAGCTTTCCCCATTGTTCGTAG3') is administered at a concentration of 2.5 mg per Kg body weight by intravenous injection into one group of mice. Control mice are injected with a control oligonucleotide. After 30 days the lungs are removed and the expression of the epithelial protein monitored by immunoassay, or by Northern or Southern blot analysis. hnRNP expression and tumor growth rate are expected to be lower in those mice receiving injections of antisense oligonucleotides than those receiving injection of the control oligonucleotide.

EXAMPLE 7

Inhibition of Epithelial Protein Expression in Human Cells

Inhibition of epithelial protein expression in human cells may be shown as follows. NCI-H720 human lung carcinoid cancer cells are grown in R5 medium. Antisense oligonucleotides having the nucleic acid sequence 5'TAAGCTTTC-CCCATTGTTCGTAGT3' are resuspended in phosphate buffered saline and mixed with DOTAP (Boehringer Mannheim), a lipofection reagent (2.5 $\mu$g/ml of culture medium) at the desired concentration. Fresh antisense oligonucleotide, in the absence of DOTAP, is added after 16–20 hrs of incubation. After 26–40 hours the cells are rinsed in serum-free media lacking both methionine and cysteine and label added for 4 hours in 1 ml of medium containing 150–200 $\mu$Ci$^{35}$S-translabel (ICN). The medium is collected.

Immunoprecipitates are recovered after incubation with 703D4 antibody electrophoresed and autoradiographed. The epithelial protein expression is expected to be lower from human cells treated with antisense oligonucleotides than human cells treated with a control oligonucleotides.

EXAMPLE 8

Expression of Early Lung Cancer Detection Marker P31 in Neoplastic and Non-Neoplastic Respiratory Epithelium

Materials and Methods

Tissues

Twenty-eight paraffin-embedded, stage I NSCLC resection specimens and corresponding pathology reports from 28 patients were obtained from the Department of Pathology, Naval Hospital, Bethesda, Md. as part of an approved clinical protocol (22). All material was reviewed by the study's reference pathologist (R.I.L.) and tumors were diagnosed according to the WHO classification (23). For each patient, one representative tissue block was chosen and the morphologic status of the respiratory epithelium in three lung compartments (bronchi, bronchioli, alveoli) was recorded. P31 status was evaluated relative to the field changes in the airways adjacent to the primary tumor contained in the paraffin block.

Immunohistochemistry

703D4 (5) was purified from mouse ascites using a Protein A column and discontinuous glycine NaCl/citrate gradient (Pierce, Rockford, Ill.). 10 µg/ml of Protein A purified mouse monoclonal antibody was used to identify areas of p31 expression. Immunohistochemical staining was performed using the Vectastian ABC kit (Vector Laboratories, Burlingame, Calif.) following the vendor's instructions with previously reported modifications (11). All experiments incorporated a tumor slide known to express p31 as a positive control and an isotopic (IgG 2b) myeloma protein (Sigma Chemical Co., St. Louis, Mo.) as a negative control.

Procedure for Slide Analysis

Three distinct lung compartments (bronchi, bronchioli, and alveoli) were mapped for each case using light microscopy in corresponding hematoxylin and eosin stained sections. These compartments were differentiated by their epithelium and surrounding tissue as previously described (12). All slides were screened for the presence of the following histologic abnormalities: basal cell hyperplasia (BCH); goblet cell hyperplasia (GCH); squamous metaplasia (SQM), dysplasia (DYS); type II cell hyperplasia (T2H); fibrosis (FIB) and bronchiolization of the alveoli (BOA) (Table I). These morphologic designations were determined by concurrence of three reviewers (J. Z., S. M. I., R. I. L.) using published criteria (9,13,14).

To quantitate abnormalities in each compartment, the number of HPFs containing the abnormality was divided by the total number of fields analyzed. All individual representatives of the bronchial and/or bronchiolor compartments contained in each section was analyzed. Each slide was designated as having one alveolar region. In alveoli containing abnormalities, a total of 10 high power fields (HPFs) per slide using a 40× objective of the microscope was sampled and counted. In bronchi and bronchioli, it was not always possible to evaluate 10 HPFs of abnormalities, therefore as many HPFs as possible were included. For instance, in one bronchus 3 HPFs of BCH in a total of HPFs (Table II) were counted. For comparison between regions, the staining index (SI, see below) for areas of related histology (ARH) was averaged, that is, for each histological abnormality and for normal epithelium in each lung compartment.

Levels of p31 expression were scored in normal and atypical lung compartments as well as corresponding tumor tissue independently by two readers (J. Z., S. M. J.). Discrepancies were resolved after joint review prior to clinical correlation analysis. A staining distribution score (0=no positive cells; 1 for 1–10%; 2 for 11–50%; 3 for 51–100% of cell positive) and staining intensity score (0=negative, 1=+; 2=++; 3=+++) was obtained for each patient. Using the sum of these values, an SI (SI=distribution score+intensity score, possible values: 0, 2–6) was established for each lung compartment as previously published (15) (Table 4).

TABLE 4

SCORING CRITERIA FOR P31 EXPRESSION

| Staining Index[1] (0, 2–6) | Staining pattern | Cellular Localization |
|---|---|---|
| Negative = (0) | Focal = (F) | Cytoplasmic |
| Weak = (2) | Diffuse = (D) | Membranous |
| Moderate = (3–4) | | Perinuclear |
| Strong = (5–6) | | |

[1]Staining index (SI) = Sum of distribution of and intensity scores were distribution scores equals the percent of positive epithelial cells in high power field (0 = no positive cells; 1 for 1–10%; 2 for 11–50%; 3 for 51–100% of cells positive) and intensity of staining (0 = negative, 1 =+; 2 = ++; 3 = +++).

Clinicopathologic Analysis

Data were obtained from 28 patients. SI data for all compartments examined were averaged to yield one value per patient per compartment. Comparisons of SIs were performed between various subgroups using Wilcoxon rank sum test. All p-values are two-sided.

EXAMPLE 9

Results

Distribution of Normal vs Abnormal Lung Compartments

From the 28 NSCLC cases examined, we identified 11 bronchi in 6 specimens, 40 bronchioli in 21 specimens, and 24 alveolar regions in 24 specimens. Twenty-seven of the 28 specimens were included in the analysis since they contained both tumor and non-neoplastic lung tissue (one specimen contained only tumor with no recognizable non-neoplastic tissue). The presence of histologic abnormalities in each lung compartment was then screened. BCH, GCH and DYS was detected in 3, 2 and 1 bronchi respectively, however no areas of SQM were detected in any of the specimens examined. In bronchioli, only 7 of 40 were found to contain histologic abnormalities. Of the 24 specimens with alveolar tissue, 7 contained histologically normal alveoli and 17 contained one or more abnormality. T2H was the most common histologic abnormality observed (15/24), while BOA was detected in only 3 of the 24 cases (2 of which also contained T2H) and one alveolar compartment contained FIB. A summary of histologic abnormalities detected in the various lung compartments are shown in Table 5.

TABLE 5

DISTRIBUTION OF HISTOLOGIC ABNORMALITIES
IN NON-NEOPLASTIC LUNG (N = 27)[1]

| Compartment Number (n)[2] | Number of normal (%) | Number of ARHs with abnormalities (Number of HPFs with abnormality/Total number of HPFs)[3] | | | | | |
|---|---|---|---|---|---|---|---|
| | | BCH | GCH | SQM | DYS | T2H | BOA |
| BRONCHI (11)[4] | 6 (55%) | 3 (8/21) | 2 (20/20) | — | 1 (8/10) | — | — |
| BRONCHIOLI (40) | 33 (82%) | 1 (2/3) | — | — | 6 (24/27) | — | — |
| ALVEOLI (24)[4] | 7 (29%) | — | — | — | — | 15 (80/160) | 3 (6/160) |

Figure 11A:
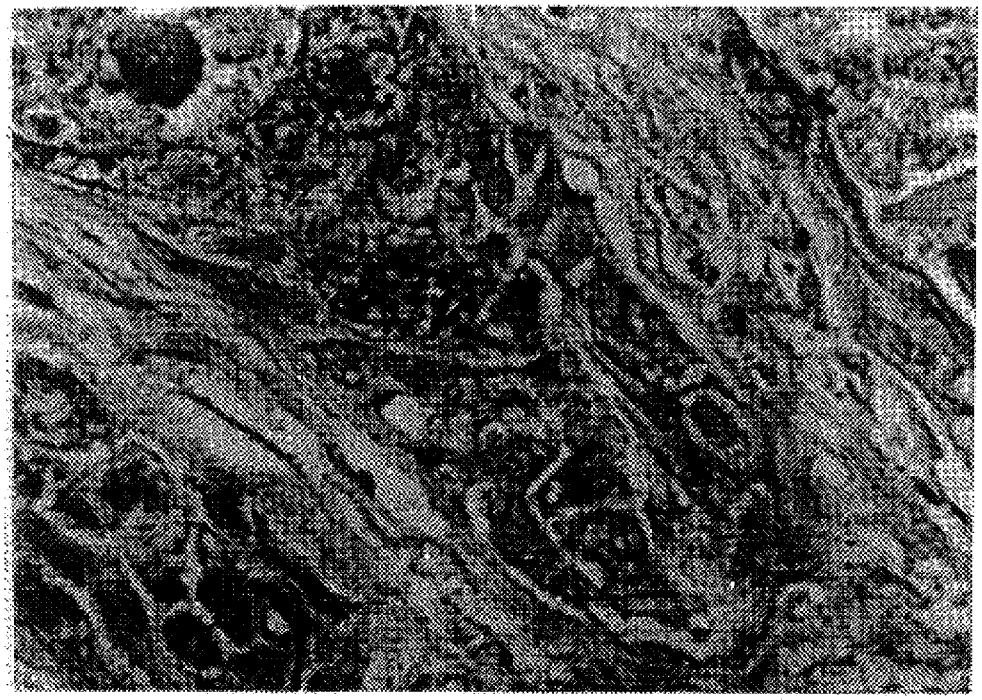
FIGS. 11A through 11C shows P31 expression pattern in primary NSCLC 6A) Focal cytoplasmic p31 staining in squamous cell carcinoma (Immunohistochemical staining, X360). 11B) Diffuse p31 expression with granular staining in an adjacent area at pulmonary adenocarcinoma. Note perinuclear staining pattern, inset. (Immunoperoxidase, X360). 11C) Pulmonary adenocarcinoma with membranous expression pattern (Immunoperoxidase, X270).
Figure 11B:
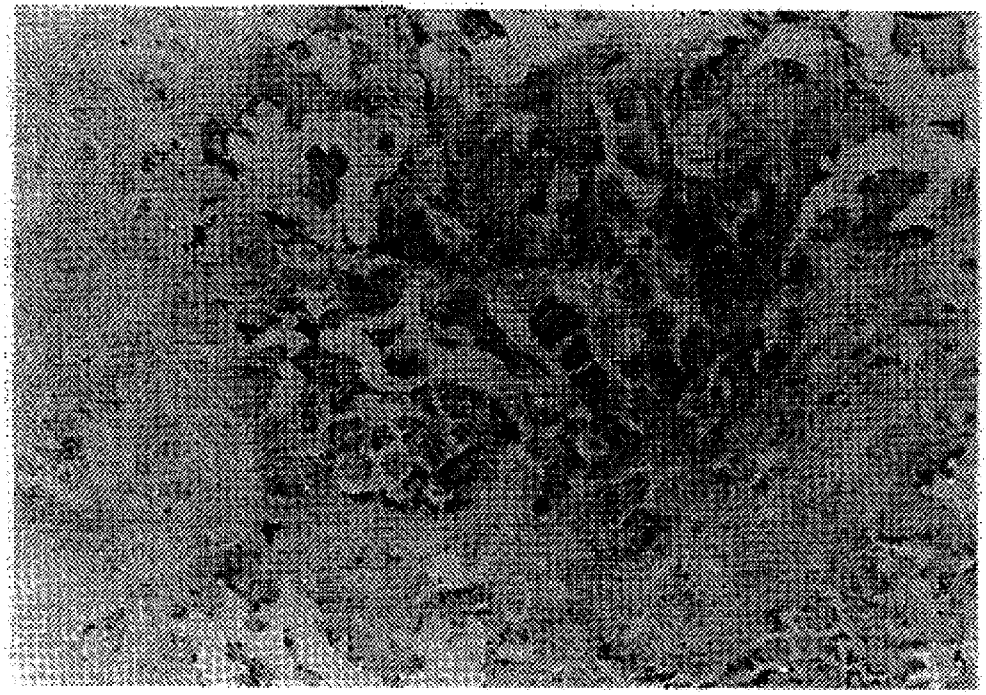
Figure 11C:

Abbreviations:
BCH = basal cell hyperplasia, GCH = goblet cell hyperplasia, SQM = squamous metaplasia, DYS = dysplasia, T2H-type II hyperplasia, BOA-bronchiolization of the alveoli
[1]Number of patients specimens, one of the 28 slides lacked non-neoplastic lung tissue
[2]Number of areas of related histology (ARHs) analyzed
[3]ARHs = Areas of related histology
[4]Some compartments contained more than one abnormality.

p31 Expression in NSCLC p31 expression in a range of NSCLC subtypes are tabulated in Table 6. Of the 28 primary lung tumors, 16 (57%) demonstrated p31 immunoreactivity. p31 expression in all histologic subtypes except the single carcinoid examined was observed. Both focal (detected in solitary cell or small groups of tumor cells) and diffuse (≧50% of tumor cells positive) staining was observed. The predominant staining pattern was diffuse and cytoplasmic as illustrated in FIGS. 11a and 11b. In addition to the predominantly cytoplasmic staining pattern, membranous staining was observed in 1 of the 9 adenocarcinomas (FIG. 11c) and the 1 pulmonary blastoma. No correlation was apparent between staining pattern, mean staining index and tumor histology.

TABLE 6

P31 EXPRESSION IN NSCLC

| Histology | Total | Number of Positive tumors[1] | Mean Staining Index ± SEM | Staining pattern[2] |
|---|---|---|---|---|
| ADENO[3] | 16 | 9 | 2.4 ± 0.55 | D/C (8), D/C M P(1) |
| LARGE CELL | 3 | 3 | 3.0 ± 0.58 | D/C (2), F/C (1) |
| SQUAMOUS | 5 | 2 | 1.2 ± 0.8 | D/C (1), F/C (1) |
| MIXED | 2 | 1 | 2.0 ± 1.98 | D/C (1) |
| CARCINOID | 1 | 0 | 0.0 | — |
| OTHER[4] | 1 | 1 | 4.0 | D/C M P, F/C (1) |
| Total | 28 | 16 | 2.2 ± 0.09 | D/C (14), F/C (3), D/M (2), D/P (1) |

[1]A tumor with staining index ≧ 2 was called positive.
[2]Abbreviations, D = diffuse, F = focal, C = cytoplasmic, M = membranous, P = perinuclear, Some tumors demonstrated more than one staining pattern
[3]Adenocarcinoma subtypes included: Papillary and bronchioalveolar (11), Moderately differentiated (3) and Poorly differentiated (2). One of the adenocarcinomas had a small cell lung cancer compartment next to a papillary component which was negative.
[4]Pulmonary blastoma.

p31 Expression in Non-Neoplastic Lung

Results of p31 staining in normal and atypical lung compartments are summarized in Table 7. While p31 staining was not detected in histologically abnormal bronchi and bronchioli, patterns of diffuse and/or focal cytoplasmic p31 staining was expressed in one third of morphologically normal bronchi and bronchioli. More specifically, p31 expression was detected in both ciliated and non-ciliated epithelial cells as well as underlying basal cell epithelium (FIGS. 12a, 12b). While only 2 of 27 cases demonstrated well preserved bronchial glands, both demonstrated strong granular staining for p31 (FIG. 12c).

TABLE 7

P31 EXPRESSION IN NON-NEOPLASTIC LUNG

| Histology | Number of Positive ARH[1]/total ARH [Pattern][2] | | | | | |
|---|---|---|---|---|---|---|
| of Adjacent | Bronchi (n = 11)[4] | | Bronchioli (n = 40) | | Alveoli (n = 24) | |
| Tumor (N)[3] | Normal | Atypia[5] | Normal | Atypia[5] | Normal | Atypia[6] |
| Adeno (16) | 0/2 | 0/5 | 6/21 [D/C] | 0/7 | 1/5 [F/C] | 2/10 [D/C, D/M] |
| Large cell (3) | — | — | 0/4 | — | 0/1 | 0/1 |
| Squamous (5) | 0/2 | — | 4/5 [3F/C, 1D/C] | — | — | 2/4 [D/M, F/C] |
| Mixed (2) | 1/1 [D/C] | — | 1/2 [D/C] | — | — | 1/2 [D/C] |
| Carcinoid (1) | — | — | 0/1 | — | 0/1 | — |
| Other[7] (1) | 1/1 [F/C] | — | — | — | — | — |
| Total (%) | 2/6 (33) | 0/5 (0) | 11/33 (33) | 0/7 (0) | 1/7 (4) | 5/17 (29) |

[1]All ARH with staining index $\geq$ 2 were scored positive.
[2]Abbreviations, D = diffuse, F = focal, C = cytoplasmic, M = membranous
[3](N) = number of patient specimens.
[4](n) = number of lung compartments
[5]Basal cell hyperplasia, goblet cell hyperplasia, dysplasia
[6]Fibrosis, type II hyperplasia, bronchiolization of the alveoli
[7]Pulmonary blastoma p31 expression in alveolar epithelium was confined to type II cells (FIG. 12d) and was most remarkable in areas containing T2H (FIGS. 13a and 13b) which were frequently accompanied by fibrosis. In contrast, areas containing BOA were negative (not shown). Since p31 staining was most remarkable in alveoli, p31 immunoreactivity in two patient groups was compared, one with histologically normal alveolar regions (n=5) and the other with T2H (n=15). Only 1 of 5 patients demonstrated p31 staining in the group with normal alveoli, as compared to 5 of 15 patients which had positive p31 staining in regions containing T2 H. A stronger staining intensity was observed in alveolar regions containing T2H (FIGS. 13a and 13b) when compared to normal alveolar regions (FIG. 12d). When the mean SI of normal alveolar epithelium (0.36±0.36) to T2H (1.09±0.45) was compared, no statistically significant difference (p=0.37, Wilcoxon rank sum) was found. Both diffuse and focal cytoplasmic staining were seen in alveoli, however, membranous staining was occasionally observed in alveoli containing T2H (FIG. 13b).

Comparison of p31 Expression in Tumor vs Non-neoplastic Lung

A comparison of p31 immunoreactivity in tumor versus surrounding non-neoplastic lung is illustrated in Table 8. Of the 27 specimens analyzed, 15 contained p31 positive tumor tissue, 7 of which (47%) also demonstrated p31 staining in the surrounding non-neoplastic lung (most frequently in alveolar region) and the remaining 8 specimens (53%) showed no antigen expression in non-neoplastic lung. Alternatively, in 3 of 12 cases where the tumor tissue did not express p31, the surrounding non-neoplastic tissue-was positive for p31 expression (25%). There was no significant association between p31 expression in tumor and nonneoplastic lung (p2=0.42, Fisher's exact test).

TABLE 8

Comparison Of p31 Expression In Tumor vs. Non-neoplastic Lung

| TUMOR (27)[1] | NON-NEOPLASTIC LUNG (27) | |
|---|---|---|
| | POSITIVE | NEGATIVE |
| POSITIVE (15) | 7 | 8 |
| NEGATIVE (12) | 3 | 9 |

[1]One of the 28 slides lacked non-neoplastic lung tissue.

Clinicopathological Correlation:

p31 expression in various lung compartments was evaluated for association with clinicopathologic features such as smoking history (pack years), sex and age. No correlation could be found between p31 expression and gender (Table 9).

TABLE 9

Relationship of p31 expression status and clinical features (age)

| | | | NUMBER OF PATIENTS WITH STAINING INDEX $\geq$ 2/TOTAL NUMBER OF PATIENTS (MEAN STAINING INDEX ± SEM) | | | |
|---|---|---|---|---|---|---|
| Sex | Years Range | (N)[1] | Bronchi | Bronchioli | Alveolar Region | Tumor |
| Males | $\leq$59 | (6) | 0/2 (0) | 0/8 (0) | 0/9 (0) | 5/10 (1.90 ± 0.66) |

TABLE 9-continued

Relationship of p31 expression status and clinical features (age)

| | | | NUMBER OF PATIENTS WITH STAINING INDEX ≥ 2/TOTAL NUMBER OF PATIENTS (MEAN STAINING INDEX ± SEM) | | | |
|---|---|---|---|---|---|---|
| Sex | Years Range | (N)[1] | Bronchi | Bronchioli | Alveolar Region | Tumor |
| | ≧60 | (11) | 1/2 (2.0 ± 2.0) | 3/5 (1.6 ± 0.68) | 2/6 (1.08 ± 0.79) | 4/7 (1.71 ± 0.68) |
| | | $p_2 =$ | 0.62 | 0.023 | 0.09 | 0.92 |
| Females | ≦59 | (3) | 0/2 (0) | 0/4 (0) | 1/5 (0.4 ± 0.4) | 4/6 (3.0 ± 0.97) |
| | ≧60 | (8) | 1/1 (2.0) | 2/4 (2.3 ± 1.35) | 3/4 (2.58 ± 0.93) | 3/5 (2.4 ± 0.98) |
| | | $p_2 =$ | 0.48 | 0.19 | 0.08 | 0.49 |
| Males | All ages | (17) | 1/4 (1.0 ± 1.0) | 3/13 (0.62 ± 0.33) | 2/15 (0.43 ± 0.33) | 9/17 (1.82 ± 0.46) |
| Females | All ages | (11) | 1/2 (0.67 ± 0.67) | 2/8 (1.15 ± 0.76) | 4/9 (1.37 ± 0.58) | 8/11 (2.73 ± 0.66) |
| | | $P_2 =$ | 0.83 | 0.73 | 0.11 | 0.21 |

[1](N) = Number of patients.

There was a statistically significant association of p31 expression status with smoking history and age. A significant increase in p31 expression was observed in heavy smokers (>50 pack years) in bronchioli ($P_2=0.021$). A statistically significant increase in p31 expression in bronchioli ($P_2=0.005$) and alveoli ($P_2=0.017$) of older patients (Table 10) was found. This increase in p31 expression with smoking history and age only reached significance (p<0.05) when males and females were grouped together, but appears as a nonsignificant increase (trend) for each sex separately.

To determine if p31 expression identifies potentially important preneoplastic cell populations, we focused on p31 immunoreactivity in non-neoplastic lung was focused on. p31 was most commonly expressed in areas of T2H, which may reflect changes in the biology of this common cell type suggesting that T2H is a candidate preneoplastic change. This may be particularly relevant because the histopathology of lung cancer has been changing recently, with adenocarcinoma increasing in the United States. Pulmonary adenocarcinomas commonly demonstrating papillolepidic fea-

TABLE 10

Relationship of p31 expression status with smoking history & age

| Clinical Features | Total Number of Cases | Mean staining Index[1] ± SEM (Number of Specimens) | | | | | | | |
|---|---|---|---|---|---|---|---|---|---|
| | | Bronchi | | Bronchioli | | Alveolar Region | | Tumor | |
| Pack Years | | | | | | | | | |
| ≦50 | 14 | 0.4 ± 0.4 | (5) | 0 | (10) | 0.2 ± 0.2 | (10) | 2.71 ± 0.52 | (14) |
| >50 | 14 | 2.0 ± 2.0 | (2) | 1.56 ± 0.59 | (11) | 1.2 ± 0.48 | (14) | 1.64 ± 0.55 | (14) |
| | $p_2 =$ | 0.47 | | 0.021 | | 0.14 | | 0.2 | |
| Age | | | | | | | | | |
| ≦59 | 16 | 0 | (4) | 0 | (12) | 0.14 ± 0.14 | (14) | 2.31 ± 0.55 | (16) |
| ≧60 | 12 | 2.0 ± 1.15 | (3) | 1.9 ± 0.67 | (9) | 1.68 ± 0.62 | (10) | 2.0 ± 0.55 | (12) |
| | $p_2 =$ | 0.12 | | 0.005 | | 0.017 | | 0.65 | |

[1]Mean staining index was calculated to yield one value per patient per subcompartment.

The studies have shown the presence of p31 immunoreactivity in all major histologic subtypes of tumors. p31 expression was also found in all three compartments (bronchi, bronchioli, alveoli) of respiratory epithelium. The findings demonstrated that the p31 expression pattern in NSCLC and nonneoplastic lung was variable. Both diffuse and focal staining mostly in the cytoplasm and occasionally on the cell membrane was observed. In this analysis p31 immunoreactivity was found more frequently in patients over 55 years and individuals with prolonged smoking history.

tures are thought to arise from progenitor cells in the peripheral airways, namely the Clara cells and type II pneumocytes. Yet, preneoplastic histologic abnormalities found in the peripheral airways (bronchioli and/or alveoli) are not well defined. The fact that normal appearing type II cells can express the p31 early lung cancer detection marker may be indicative of the initial transformation to a precancer state.

In contrast, well-defined histologic abnormalities such as BCH, GCH, SQM are frequently seen in conducting airways (bronchi and bronchioli); however, all of these histologic changes are potentially reversible (14). SQM was not detected in any of the specimens analyzed in this study. This was most likely due to the limited amount of material available for study. The absence of SQM and lack of p31 staining in histological abnormalities of airways in general may reflect the reversible nature of these lesions. We have previously shown that p31 expression is absent in human lung tissue obtained from young, non-smoking trauma victims. Therefore, the presence of p31 immunoreactivity in histologically normal epithelium may actually indicate an early event preceding cytomorphological change in conducting airways.

According to the stem cell hypothesis, a single cell can differentiate along three paths to give rise to normal lung as well as the major histologic types of lung cancer (24). Since p31 can be detected in all major types of lung cancer the expression of p31 may be an early event in lung carcinogenesis. As reported in Table V there were 3 specimens which did not express p31 but p31 was still expressed in the surrounding non neoplastic epithelium.

p31 expression occurs throughout the human lung in both non-neoplastic and neoplastic tissue from patients who had Stage I NSCLC resections with curative intent. The distinct expression pattern makes p31 an informative marker for potentially neoplastic events such as peripheral adenocarcinomas originating in the alveolar region of human lung. Increased p31 expression was found to be associated with T2H, increased age and prolonged smoking history.

EXAMPLE 10

Fluorescence In Situ Hybridization Using Production Iodide Counterstaining for Detection of Expression of Epithelial Protein mRNA Fluorescence in situ hybridization (FISH) in combination with propidium iodide (PI) counterstaining is used to demonstrate mRNA expression of epithelial protein, peptides or variants in bone sections as described by Wulf, M. et al. *Biotechniques*, Vol. 19, No. 3, pp.368–372, 1995.

After surgical removal, tissue samples are immediately fixed in 10% formaldehyde (pH 7.0) and nondecalcified, paraffin-embedded specimens are used for FISH. Pretreatment of sections before hybridization is carried out as described by Sandberg, M. et al., *J. Bone Joint Surg.*, 71:69–71, 1989. For prehybridization, sections are covered with 300 µl of prehybridization buffer (50% deionized formamide, 0.3 M NaCl 10 mM Tris-HCl, pH 7.5; 10 mM NaHPO$_4$, pH 6.8; 5 mM EDTA; 0.1×Denhardt's 10 mM dithiothreitol; 0.25 mg/ml yeast tRNA [Sigma Chemical, St. Louis, Mo.]; 12.5% dextran sulfate; 0.5 mg/ml salmon sperm DNA [Sigma Chemical] and is incubated in a humid chamber for 2 hr at 42° C. For hybridization, a digoxigenin-labeled double-stranded cDNA probe for the epithelial protein having the sequence 5'-GAGTCCGGTTCGTGTTCGTC-3' (SEQ ID NO.: 11) and 5'-TGGCAGCATCAACCTCAGC-3' (SEQ ID NO.:12) are used. The probe is labeled with digoxigenin according to the protocol of the Dig-Labeling Kit (Boehringer Mannheim, Mannheim, Germany). Prior to hybridization, the labeled probe is mixed with prehybridization buffer to a concentration of 1 µg/mL, heated for 10 min. at 95° C. and quickly chilled on ice. Excess prehybridization buffer is removed from the slides, and approximately 30 µl of hybridization solution is applied to the sections. Sections are covered with a coverslip, sealed with rubber cement and hybridized in a humid chamber at 42° C. for 18 h. The post-hybridization washing steps are performed as described by Weithege, T., et al. *Pathol. Res. Pract.*, 187:912–915, 1991.

Probe detection is carried out using an anti-digoxigenin antibody conjugated to FITC (fluorescein isothiocyanate; Boehringer Mannheim). Unbound conjugate is removed by washing two times for 10 min. with phosphate-buffered saline (PBS) (3.8 mM NaH$_2$PO$_4$; 7.8 mM Na$_2$HPO$_4$; 0.13 M NaCl). Sections are counterstained with PI (Boehringer Mannheim) in PBS (500 ng/mL) for 5 min. at room temperature (30 µl per section). Excess PI is removed by washing with PBS, followed by dehydration (70%, 96%, 100% ethanol). Sections are air-dried and mounted in a glycerol/PBS solution. For analyses, a fluorescence microscope (Leitz Diaplan, Wetzlar, Germany) is used.

Using FISH, differential expression of the epithelial protein, peptide or variant mRNA in precancer and cancer cells is determined as compared to normal cells.

EXAMPLE 11

In Situ PCR and In Situ RT-PCR of Paraffin-Embedded Lung Sections for Localization of Nucleic Acids of an Epithelial Protein The following protocol as described by Martinez, A., et al. *J. Histochem. and Cytochem.*, Vol. 43, No. 8, pp.739–747, 1995 is used to detect nucleic acids of the epithelial protein, peptide or variants thereof which are associated with precancer and cancer, in precancer and cancer cells. The method is also useful to detect the chromosomal location of the nucleic acid or 10 chromosomal abnormalities at the location as has been reported by Saccone, S. et al *Genomics*, Jan. 12, 1992 (1): 171–174; Biamonti, G. et al *Nucleic Acid Res.*, Jun. 22, 1994 (11):1996–2002.

Materials and Methods
Cell Lines

NCH720 and NCH157 cell lines are used in this study. These cell lines were grown under protein-free and hormone-free conditions using phenol red-free RPMI-1640 containing 30 nM selenium and 10 mM L-glutamine (Siegfried et al., *J. Biol. Chem.* 269:8596, 1994). Pellets of approximately 5×10$^6$ cells are washed in PBS, re-suspended in 1 ml of 2% NuSieve low melting-point agarose (Cat. 50082, Lot 626592; FMC BioProducts, Rockland, Me.), allowed to solidify, fixed for 2 hr in 4% paraformaldehyde or 10% formalin, and embedded in paraffin by routine histopathology techniques.
Archive Books Ten formalin-fixed, paraffin-embedded blocks containing normal lung and representative cases of precancer and lung tumors are obtained from the files of the BPRB, NCI at the NCI-Navy Medical Oncology Branch.
Immunohistochemistry The monoclonal antibody 703D4 is used (U.S. Pat. No. 4,569,788). A avidin-biotin histochemical staining procedure (Hsu et al, *J. Histochem. Cytochem.* 29:577, 1981) is used to localize 703D4 immunoreactivity in lung tissue and cell lines using the Vectastrain ABC kit (Cat PK-4001; Vector Laboratories, Burlingame, Calif.) with a 0.03% solution of 3,3'-diaminobenzidine (Cat. D-5637, Lot 12H3642; Sigma, St. Louis, Mo.) and 0.006% H$_2$O$_2$ as the enzyme substrates.
RNA Extraction The guanidine isothiocyanate-cesium chloride method of Glisin et al., (*Biochemistry* Vol. 13;2633, 1974) is used to extract total RNA from the cell lines. Poly A+RNA from normal human brain (Cat. 6516-2, Lot 2Y081), liver (Cat. 6510-2, Lot 39076), lung (Cat. 6524-2, Lot 34401), stomach (Cat. 6548-2, Lot 38131), and uterus (Cat. 6537-2, Lot 29100) are purchased from Clontech Laboratories (Palo Alto, Calif.).

Northern Blot

Standard formaldehyde gels were run with total RNA (10 µg/well) at 120V. 100 mAmp for 3 hr. At the end of the run, the gels are washed for 15 min in 20×SSC and then blotted overnight by capillary flow transfer onto a 0.45-µm nitrocellulose filter (Davis et al, *Basic Methods in Molecular Biology*, Norwalk, Conn., Appleton & Large, 1986). The blots are UV crosslinked at 1200 Joules and pre-hybridized for 4 hr. The Stratagene Prime-It kit (Stratagene; La Jolla, Calif.) is used to label the probe. The probes were prepared by random priming of inserts gel purified from restriction endonuclease digests of plasmids containing full-length cDNAs for hnRNP-A2 and A1 with $^{32}$P-dCTP. Probe (1×10$^6$ cpm) is added to each ml of hybridizing buffer. After overnight hybridization, the blot is washed once in 2×SSC/0.1% SDS at room temperature, the blot is washed once in 2×SSC/0.1% at room temperature (RT; 30 min) and once with 0.1% SSC/0.1% SDS at 60° C. (30 min). The blots are then air-dried and autoradiographed at −80° C. on Kodak XAR5 film for 1–2 days.

Standard PCR

Oligonucleotide primers for epithelial protein are made using a MilliGen 8700 DNA synthesizer (Millipore; Marlborough, Mass.). Sequences are 5'-GAGTCCGGTTCGTGTTCGTC-3' (SEQ ID NO.: 11 and 5'-TGGCAGCATCAACCTCAGC-3' (SEQ ID NO.: 18. All buffers, enzymes, and nucleotides used are obtained from Applied Biosystems (Perkin-Elmer Cetus; Norwald, Conn.). A Perkin-Elmer 9600 Thermocycler is used to amplify the samples. PCR products are analyzed electrophoretically using a 1% agarose gel (80 V, 3 hr) and the ethidium bromide staining is observed under UV light, followed by Southern analysis with nested $^{32}$P-labeled probes.

Southern Analysis

Gels are denatured in 1.5 M NaCl/0.6 M NaOH and 1.5 M NaCl/2 M Tris and blotted onto a 0.2-µm nitrocellulose filter in 20×SSC by capillary flow transfer overnight. The filter are cross-linked at 80° C. under vacuum and put in hybridization buffer. Anti-sense nested probes are end-labeled by standard $^{32}$P procedures (Sambrook et al, *Molecular Cloning: A Laboratory Manual*, Vol. II, Cold Spring Harbor, N.Y., Cold Spring Harbor Laboratory Press, 8.3, 1989). Hybridization with the probe is done overnight at 42° C. Stringency washing at RT is in 5×SSC/0.1% SDS (twice for 30 min), then 1×SSC/0.1% SDS (twice for 30 min). Filters are air-dried and autoradiographed at −80° C. on Kodak XAR5 film for 2–4 hr.

In Situ PCR

The in situ PCR technique for localizing specific DNA sequences is performed by a three-step protocol as described by Nuovo (PCR in situ hybridization, In Nuovo, G J, ed. PCR In Situ Hybridization: Protocols and Applications, New York, Raven Press, 157, 1992a). After dewaxing the tissue sections, a protein digestion is carried out to facilitate reagent penetration into the cells. The second step consists of the PCR itself with simultaneous labeling of the PCR products, followed by the third step that visualizes the labeled product. The in situ amplification technique for RNA detection utilizes a similar protocol. However, it incorporates two additional steps. After proteinase digestion the tissue is exposed to RNAse-free DNAse to avoid amplification of genomic DNA. Second, the remaining mRNA is reverse-transcribed to form cDNA templates, which are in turn amplified by PCR. To maximize the efficiency of the in situ PCR technique, all of these protocol steps must be optimized for individual experiments. The reverse transcription and the PCR steps is performed using an OmniSlide thermocycler (20-slide capacity) equipped with a heated wash module (National Labnet; Woodbridge, N.J.).

Protease Digestion

Depending on the fixative and the nature of the tissue, reagent access to the target nucleic acid can vary. To identify optimal permeability methods, we analyzed enzyme digestion procedures, may be varied by the concentration of proteinase K (Cat. P-0390, Lot 93H0603; Sigma) between 1 and 100 µg/ml and incubation time (5–45 min).

DNAse Digestion

Deoxyribonuclease I Amplification Grade (Cat. 18068-015, Lot ED2409; Gibco BRL, Gaithersburg, Md.), 10 U/slide is used to degrade the DNA according to the manufacturer's specifications. The influence of different digestion times on the quality of the staining is tested.

Reverse Transcription

For this step the SuperScript Preamplification System (Cat. 18089-011, Lot EDT001; Gibco is used following the manufacturer's specifications. In summary, the sections are immersed in a solution containing the random primers, covered with parafilm coverslips, and incubated in the thermocycler for 10 min at 70° C. After removing the coverslips, another solution containing the reverse transcriptase (100 U/section) is added and covered with a new piece of parafilm. The slides are then maintained at RT for 10 min, at 45° C. for 45 min, and at 70° C. for 10 min.

PCR

Before the in situ PCR experiment, all parameters for the PCR reaction, including $MgCl_2$ concentration, pH, and annealing temperature, is optimized by standard PCR. At this point the PCR products can be cloned and sequenced to confirm identity. Products are cloned into a pCRII vector (Cat. 2000-01; Invitrogen, San Diego, Calif.) and sequenced with the dsDNA Cycle Sequencing Kit (Cat. 81965A, Lot CAC 108; Gibco). Optimization of conditions favoring single band production is advised because it is not possible to distinguish PCR products of different molecular weights in the tissue sections. To eliminate the possibility of generating PCR products from genomic DNA, it is important to design primers that bridge introns so as to distinguish template source on the basis of product size.

Synchronized "hot start" PCR (Nuovo, The hot start polymerase chain reaction, In Nuovo, G J, ed. PCR In Situ Hybridization Protocols and Applications, New York, Raven Press, 63, 1992b) is achieved using the Taq neutralizing antibody technique (Kellogg et al, *Bio Techniques* 6:1134, 1994). Taq-blocking monoclonal antibody was purchased from Clontech (TaqStart antibody; Cat. 5400-1, Lot 47656).

For the analyses described here the following PCR mixture is used: 2.5 mM MgCl, 200 µM dNTP2, 100 µM digoxigenin-11-2'-deoxyuridine-5'-triphosphate (Cat. 1558 706, Lot 13945241-12; Boehringer Mannheim, Indianapolis, Ind.), 1 ng/µl primers, 50 mM KCl, 10 mM Tris-HCL, pH 8.3. An 80-µl aliquot of solution is applied to each slide, and then each slide is covered by silicated glass coverslips, sealed with rubber cement, and placed in the thermocycler. The targets are amplified, 15–20 cycles to obtain crisp staining. After DNA amplification, two washes in 0.1×SSC at 45° C., 20 min each, are performed to eliminate unbound nucleotides.

Development of Digoxigenin

Detection of digoxigenin-tagged PCR products is done with a kit from Boehringer Mannheim (Cat. 1210 220, Lot. 14101420-13). It involves a 2-hr incubation with an anti-digoxigenin antibody bound to alkaline phosphatase. After a thorough rinse, the appropriate substrates (nitroblue tetrazolium and 5-bromochloro-3-indolyl-phosphate) are enzymatically transformed into a dark blue precipitate. Color deposition was checked under the microscope.

Recently, it has been observed that polyvinyl alcohol enhances the intensity of the alkaline phosphatase-nitroblue tetrazolium reaction and prevents diffusion of the precipitate (Barth and Ivarie, *Bio Techniques* 17:324, 1994; De Block and Debrouwer, *Anal. Biochem.* 215:86, 1993). To take advantage of this technique the dilution of the anti-digoxigenin antibody is increased to 1:2000 (instead of the usual 1:500 recommended by the manufacturer) to obtain considerable background reduction.

Controls

The PCR technique is well known for its ability to amplify even single copies of DNA in a sample, contaminants included. Therefore, the precautions recommended for routine PCR regarding scrupulous care with cleanliness, use of a dedicated set of pipettes, and preparation of the PCR mixture away from the amplification area (Orrego, Organizing a laboratory for PCR work. In Innis M A, Gelfand D H, Sninsky J J, White, T J, eds. PCR protocols: A Guide to Methods and Applications, New York, Academic Press, 447, 1990) are also applicable for in situ PCR. In addition, working with tissue sections adds new concerns, such as heterogeneous application of reagents, bubbles, drying of the boundaries, and stability of the nucleic acids during the preparation of the samples.

At least three types of controls are recommended in every experiment to avoid false-positives or -negatives.

Positive Control

Include a section from a block that is previously positive for the same set of primers. If this is the first time that these primers are being used, include a section of a well-fixed tissue or cell line known to have a high expression of the target nucleic acid as determined by other techniques (e.g., Northern analysis, standard PCR, in situ hybridization).

Negative Control

Omission of the reverse transcription and/or RNAse treatment will yield information about nonspecific amplification of remaining nuclear or mitochondrial DNA.

Negative Control

Omission of the primers in the PCR mixture will reveal nonspecific staining due to endogenous priming: DNA fragments produced by the exonuclease activity of the DNA polymerase (Komminoth and Long, *Virchows Arch* [B] 64:67, 1993) or by apoptosis (Gold et al, *J. Histo Chem. Cytochem* 41: 1023) and other artifacts such as intrinsic alkaline phosphatase activity.

An additional control consists of establishing existing relationships between the transcriptional/translational products. This can be done by staining one section for the nucleic acid by in situ PCR and a serial section with a specific antibody against the polypeptide. The co-localization of the mRNA and its protein within the same cells will strengthen the validity of the observation.

Confirmation of the in situ PCR product integrity can be achieved in two ways: (a) It is possible to scrape the tissue of the glass slide after in situ PCR, to extract the DNA (TRIzol reagent, Cat. 5596UA, Lot DPU 201; Gibco), and to analyze by agarose gel electrophoresis and Southern blot with the appropriate radioactive probe. Cloning and sequencing of this product is also possible, after several additional PCR cycles to yield products without modified bases, (b) Product identity is tested by performing in situ hybridization with a $^{32}$P-labeled nested probe after the amplification. This procedure is routinely used for indirect in situ PCR (Patterson et al *Science* 260:976, 1994; Walter et al *Ann NY Acad. Sci.* 724:404, 1994).

EXAMPLE 12

Strategies to identify significant post-translational modifications of hnRNP A2/B1 can be performed in at least two ways. The previously described cyanogen bromide digest fragments are systematically evaluated for specific sites of post translational activity. Using a panel of specialized enzymes that attack a protein at the site of a specific post translational modificatons, the presence of a particular modification is revealed in comparing an enzymatically treated cyanogen bromide-treated digest fragment with a sample of the original cyanogen bromide-treated material (that is not subjected to the enzyme). For example, treatment of digests with phosphatases would reveal change in molecular weight after treatment with the enzyme by either 2D-gel electrophoresis or by mass spectrometry. These are standard approaches to the characterization of post translational changes.

REFERENCES

1. Boring, C., Squires, T., Tong, T. and Montgomery, S. Cancer statistics. Ca-A Cancer J. for Clinicians, 44: 7–26, 1994.
2. Saccomanno, G., Saunders, R. and Klein, M. Cytology of the lung in reference to irritant, individual sensitivity and healing. Acta Cytol, 14: 377–381, 1970.
3. Frost, J., Fontana, R. and Melamed, M. Early lung cancer detection: Summary and conclusions. Am. Res. Respir. Dis., 103: 565–570, 1984.
4. Tockman, M., Gupta, P., Myers, J., Frost, J. Baylin, S., Gold, E., Chase, A., Wilkinson, P. and Mulshine, J. Sensitive and specific monoclonal antibody recognition of human lung cancer antigen on preserved sputum cell: A new approach to early lung cancer detection. J. Clin. Oncol., 6: 1685–1693, 1988.
5. Mulshine, J., Cuttitta, F., Bibro, M., Fedorko, J., Fargion, S., Little, C., Carney, D., Gazdar, A. and Minna, J. Monoclonal antibodies that distinguish non-small cell from small cell lung cancer. J. Immuol., 131: 497–502, 1983.
6. Saccomanno, G., Archer, V. and Auerbach, O. Development of carcinoma of the lung as reflected in exfoliated cells. Cancer, 33: 1974.
7. Naisell, M., Auer, G. and Kato, H. Cytological studies in man and animals on development of bronchogenic carcinoma. In: E. McDowell (eds.), Cytological studies in man and animals on development of bronchogenic carcinoma., pp. 207–242, New York: Churchill Livingstone, 1987.
8. Slaughter, D., Southwick, H. and Smejkal, W. "Field cancerization" in oral stratified squamous epithelium. Cancer, 6: 963–968, 1953.
9. Auerbach, O., Stout A., Hammond, C. and Garfinkel, M. Changes in bronchial epithelium in relation to cigarette smoking and in relation to lung cancer. The New England Journal of Medicine, 265: 253–267, 1961.
10. World Health Organization. The World Health Organization histological typing of lung tumors. American Journal of Clinical Pathology, 77: 123–136, 1982.
11. Linnoila, R., Mulshine, J., Steinberg, S., Funa, K., Matthews, M., Cotelingam, J. and Gazdar, A. Neuroendocrine differentiation in endocrine and nonendocrine lung carcinoma. Am. J. Clin. Pathol., 90: 1–12, 1988.
12. di Fiore, M. Atlas of human histology. (ed), Philadelphia: Lea & Febiger, 1981.
13. Plopper, C. G. and Dungworth, D. Structure, function, cell injury and cell renewal of bronchiolar and alveolar epithelium. In: E. McDowell (eds.), Structure, function, 14. Nasiell, M. The general appearance of the bronchial epithelium in bronchial carcinoma. Acta Cytol, 7: 97–106, 1963.
15. Jensen, S., Steinberg, S. Jones, J. and Linnoila, R. Clara cell 10 KD protein mRNA in normal and atypical regions of human respiratory epithelium. Int. J. Cancer, 58: 629–637, 1994.
16. Sozzi, G., Miozzo, M., Tagliabue, E. and et al. Cytogenetic abnormalities and overexpression of receptors for growth factor in normal bronchial epithelium and tumor samples of lung cancer patients. Cancer Res., 51: 400–404, 1991.
17. Melamend, M., and Zaman, M. Pathogenesis of epidermoid carcinoma of lung. In: Y. Shimosato, M. Melamed and P. Nettesheim (eds.) Pathogenesis of epidermoid carcinoma of lung, pp. 37–64 Boca Raton, Fla.: CRC Press, 1982.
18. Hittelman, W. Wang, Z., Cheong, N., Sohn, H. and Lee, J. Premature chromosome condensation and cytogenetics of human solid tumor. Cancer Bull, 41: 298–305, 1989.
19. Carter, D., Marsch, R. and Baker, R. Relationship of morphology of clinical presentation in ten cases of early squamous carcinoma of the lung. Cancer, 37: 1389–1396, 1976.
20. Nettesheim, P. and Szakal, M. Morphogenesis of alveolar bronchiolization. Lab. Invest., 26: 210–219, 1972.
21. Tockman, M., Erozan, Y., Gupta, P., Piantadosi, S., Mulshine, J., Ruckdeschel, J. The early detection of second primary lung cancers by sputum immunostaining. Chest, 106: 385S–390S, 1994.
22. Shaw, G., Gazdar, A., Phelps. R., Linnoila, R., Ihde, D., Johnson, B., Oie, H., Pass, H., Steinberg, S., Ghosh, B., Walsh, T., Nesbitt, J., Cotelingam, J., Minna, J. and Mulshine, J. Individualized chemotherapy for patients with non-small cell lung cancer determined by prospective identification of neuroendocrine markers and in vitro drug sensitivity testing. Cancer Research, 53:5181–5187, 1993.
23. World Health Organization. The World Health Organization histological typing of lung tumors. American Journal of Clinical Pathology, 77:123–136, 1982.
24. Gazdar, A., Carney, D., Guccion, J. and Baylin, S. Small cell carcinoma of the lung: cellular organ and relationship to other pulmonary tumors. In: F. Greco, R. Oldman and J. Bunn PA (eds.), Small cell carcinoma of the lung.

We claim:

1. A method for diagnosing cancer or precancer in a patient, which method comprises:
   (a) detecting the level of heterogenous nuclear ribonucleoprotein (hnRNP) in a test biological sample comprising hnRNP obtained from the patient; and
   (b) comparing the level of the hnRNP in the test biological sample with the level of hnRNP in a normal sample obtained from the patient or from another source; whereupon a higher level of hnRNP in the test biological sample as compared to the level of hnRNP in the normal sample is indicative of the presence of cancer or precancer in the patient,
   (b) comparing the level of the hnRNP in the test biological sample with the level of hnRNP in a normal sample obtained from the patient or from another source; whereupon a higher level of hnRNP in the test biological sample as compared to the level of hnRNP in the normal sample is indicative of the presence of cancer or precancer in the patient.

2. The method according to claim 1, wherein the hnRNP comprises at least one amino acid sequence selected from the group consisting of:

| | |
|---|---|
| AARPHSIDGRVV | (SEQ. ID NO.: 1), |
| QEVQSSRSGRGG | (SEQ. ID NO.: 2), |
| REKEQFRKLFI | (SEQ. ID NO.: 3), |
| EKTKETVPLERKKRE | (SEQ. ID NO.: 4), |
| AARPSDGRVV | (SEQ. ID NO.: 5), and |
| EREKEQFRKLFI | (SEQ. ID NO.: 6). |

3. The method according to claim 1, wherein the hnRNP comprises SEQ ID NO.: 7 or SEQ ID NO.: 8.

4. The method according to claim 1, wherein the hnRNP comprises a post-translational modification.

5. The method according to claim 4, wherein the post-translational modification comprises alteration of an aromatic amino acid, methylation of an arginine, methylation of a lysine, methylation of a histidine, phosphorylation of a serine, phosphorylation of a threonine, a blocked N-terminus or glycosylation.

6. The method according to claim 1, wherein the cancer is lung cancer.

7. The method according to claim 1, wherein the patient is a human patient.

8. The method according to claim 1, wherein the biological sample is obtained from a cell or cells, a tissue or tissues, blood, serum, stool, urine, amniotic fluid, sputum or a bone tissue biopsy.

9. The method according to claim 1, wherein the cancer is breast cancer.

10. The method according to claim 6, wherein the biological sample is bronchial fluid or sputum.

11. The method according to claim 6, wherein the biological sample is respiratory epithelial cells, bronchial epithelial cells or alveolar cells.

\* \* \* \* \*